United States Patent

Banks

(10) Patent No.: US 6,268,509 B1
(45) Date of Patent: Jul. 31, 2001

(54) PARASITICIDAL PYRAZOLES

(75) Inventor: Bernard Joseph Banks, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/511,885

(22) Filed: Feb. 23, 2000

Related U.S. Application Data

(62) Division of application No. 09/319,310, filed as application No. PCT/EP97/06697 on Nov. 25, 1997, now Pat. No. 6,075,043.

(30) Foreign Application Priority Data

| Dec. 5, 1996 | (GB) | 96252903 |
|---|---|---|
| Feb. 4, 1997 | (GB) | 97022354 |
| Jun. 10, 1997 | (GB) | 97120455 |

(51) Int. Cl.⁷ .................. C07D 231/14; C07D 401/04
(52) U.S. Cl. .................. 548/375.1; 546/275.4
(58) Field of Search .................. 548/375.1; 546/275.4

(56) References Cited

U.S. PATENT DOCUMENTS

| 5,232,940 | 8/1993 | Hatton et al. |
| 5,547,974 | 8/1996 | Hatton et al. |

FOREIGN PATENT DOCUMENTS

| 0050335 | 4/1982 | (EP) |
| 0234119 | 12/1986 | (EP) |
| 0234119 | 9/1987 | (EP) |
| 0249409 | 12/1987 | (EP) |
| 0280991 | 2/1988 | (EP) |
| 0295118 | 6/1988 | (EP) |
| 0295227 | 6/1988 | (EP) |
| 0273862 | 7/1988 | (EP) |
| 0280991 | 9/1988 | (EP) |
| 0295117 | 12/1988 | (EP) |
| 0295118 | 12/1988 | (EP) |
| 0579280 | 1/1994 | (EP) |
| 0780378 | 10/1996 | (EP) |
| 0780378 | 6/1997 | (EP) |
| 1586258 | 3/1981 | (GB) |
| 2085302 | 4/1982 | (GB) |
| WO93/06089 | 4/1993 | (WO) |
| 9416732 | 8/1994 | (WO) |
| 9524219 | 9/1995 | (WO) |
| 9707102 | 2/1997 | (WO) |
| 9707202 | 2/1997 | (WO) |
| 9711602 | 4/1997 | (WO) |
| 9712521 | 4/1997 | (WO) |
| 9736483 | 10/1997 | (WO) |
| 9736484 | 10/1997 | (WO) |
| 9736485 | 10/1997 | (WO) |
| 9736486 | 10/1997 | (WO) |
| 9824767 | 6/1998 | (WO) |

OTHER PUBLICATIONS

Elkachef et al., *Chemical Abstracts*, vol. 81, No. 152095 (1974).

*Primary Examiner*—Robert W. Ramsuer
(74) *Attorney, Agent, or Firm*—Peter C. Richardson; Paul H. Ginsburg; E. Victor Donahue

(57) ABSTRACT

Compounds of formula (I)

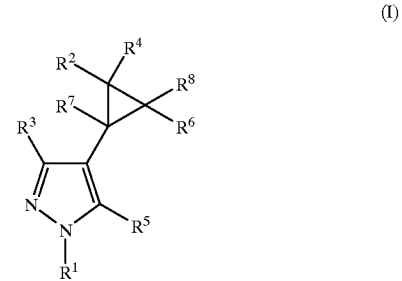

or pharmaceutically, veterinarily or agriculturally acceptable salts thereof, or pharmaceutically, veterinarily or agriculturally acceptable solvates of either entity, wherein $R^1$ is 2,4,6-trisubsituted phenyl or 3,5-disubstituted pyridin-2-yl; $R^3$ is $C_1$–$C_4$ alkyl optionally substituted with hydroxy or with one or more halo; cyano, $C_1$ to $C_5$ alkanoyl or phenyl $R^5$ is hydrogen, $C_1$ to $C_4$ alkyl, amino or halo; $R^2$ and $R^4$ are each independently selected from hydrogen, $C_1$ to $C_4$ alkyl, fluoro, chloro and bromo or, together with the carbon atom to which they are attached, form a $C_3$ to $C_6$ cycloalkyl group; $R^6$ and $R^8$ are each independently selected from hydrogen, $C_1$ to $C_4$ alkyl, fluoro, chloro and bromo; or; when $R^2$ and $R^4$ do not form part of a cycloalkyl group, $R^2$ and $R^6$, together with the carbon atoms to which they are attached, may form a $C_5$ to $C_7$ cycloalkyl group; and $R^7$ is hydrogen, $C_1$ to $C_4$ alkyl optionally substituted with one or more halo; or $C_1$ to $C_4$ alkoxy; are parasiticidal agents.

3 Claims, No Drawings

PARASITICIDAL PYRAZOLES

This present application is a divisional of U.S. Ser. No. 09/319,310, filed Jun. 3, 1999, U.S. Pat. No. 6,075,043 that represents the U.S. national stage (35 USC 371) of PCT/EP97/06697, internationally filed on Nov. 25, 1997, while claiming priority of Great Britain Specifications 9625290.3, 9702235.4, and 9712045.5, filed respectively on Dec. 5, 1996, Feb. 4, 1997, and Jun. 10, 1997. The complete text of the Ser. No. 09/319,310 application is incorporated by reference herein, as if fully set forth.

This invention relates to pyrazole derivatives having parasiticidal properties. More particularly, it relates to 1-aryl-4-cyclopropylpyrazoles.

Certain pyrazole derivatives possessing, inter alia antiparasitic activity are already known. For example, EP-A-0234119 discloses 1-arylpyrazoles for the control of arthropod, plant nematode and helminth pests. 1-Arylpyrazoles are also disclosed in EP-A-0295117; in addition to having arthropodicidal, plant nematocidal and anthelmintic activity, these compounds are reported to display antiprotozoal properties. Similar profiles of activity are also displayed by the 1-arylpyrazoles disclosed in EP-A-0295118.

The present invention provides a compound of formula (I):

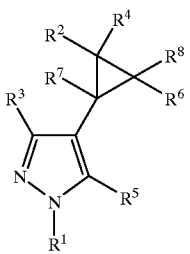

(I)

or a pharmaceutically, veterinarily or agriculturally acceptable salt thereof, or a pharmaceutically, veterinarily or agriculturally acceptable solvate (including hydrate) of either entity, wherein $R^1$ is 2,4,6-trisubstituted phenyl wherein the 2- and 6-substituents are each independently selected from halo and the 4-substituent is selected from $C_1$ to $C_4$ alkyl optionally substituted with one or more halo, $C_1$ to $C_4$ alkoxy optionally substituted with one or more halo, $S(O)_n C_1$ to $C_4$ alkyl optionally substituted with one or more halo, halo and pentafluorothio; or 3,5-disubstituted pyridin-2-yl wherein the 3-substituent is halo and the 5-substituent is selected from $C_1$ to $C_4$ alkyl optionally substituted with one or more halo, $C_1$ to $C_4$ alkoxy optionally substituted with one or more halo, $S(O)_n C_1$ to $C_4$ alkyl optionally substituted with one or more halo, halo and pentafluorothio;

$R^3$ is $C_1$ to $C_4$ alkyl optionally substituted with hydroxy or with one or more halo; cyano, $C_1$ to $C_5$ alkanoyl or phenyl;

$R^5$ is hydrogen, $C_1$ to $C_4$ alkyl, amino or halo;

$R^2$ and $R^4$ are each independently selected from hydrogen, $C_1$ to $C_4$ alkyl, fluoro, chloro and bromo or, together with the carbon atom to which they are attached, form a $C_3$ to $C_6$ cycloalkyl group;

$R^6$ and $R^8$ are each independently selected from hydrogen, $C_1$ to $C_4$ alkyl, fluoro, chloro and bromo;

or, when $R^2$ and $R^4$ do not form part of a cycloalkyl group, $R^2$ and $R^6$, together with the carbon atoms to which they are attached, may form a $C_5$ to $C_7$ cycloalkyl group; $R^7$ is hydrogen, $C_1$ to $C_4$ alkyl optionally substituted with one or more halo, or $C_1$ to $C_4$ alkoxy; and n is 0, 1 or 2.

In the above definition, unless otherwise indicated, alkyl and alkoxy groups having three or more carbon atoms and alkanoyl groups having four or more carbon atoms may be straight chain or branched chain; halo means fluoro, chloro, bromo or iodo.

The compounds of formula (I) may contain one or more chiral centres and therefore can exist as stereoisomers, i.e. as enantiomers or diastereoisomers, as well as mixtures thereof. The invention includes both the individual stereoisomers of the compounds of formula (I) together with mixtures thereof. Separation of diastereoisomers may be achieved by conventional techniques, e.g. by fractional crystallisation of chromatography (including HPLC) of a diastereoisomeric mixture of a compound of formula (I) or a suitable salt or derivative thereof. An individual enantiomer of a compound of formula (I) may be prepared from a corresponding optically pure intermediate or by resolution, either by HPLC of the racemate using a suitable chiral support or, where appropriate, by fractional crystallisation of the diastereoisomeric salts formed by reaction of the racemate with a suitable optically active acid.

Also included in the invention are radiolabelled derivatives of compounds of formula (I) which are suitable for biological studies.

The pharmaceutically, veterinarily and agriculturally acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. For a review of suitable salts, see J. Pharm. Sci., 1977, 66, 1.

A preferred group of compounds of formula (I) is that wherein $R^1$ is 2,6-dichloro-4-trifluoromethylphenyl, 2,6-dichloro-4-pentafluorothiophenyl, 2,4,6-trichlorophenyl or 3-chloro-5-trifluoromethylpyridin-2-yl; $R^3$ is methyl, ethyl, prop-2-yl, 1-hydroxyethyl, 2-hydroxyprop-2-yl, difluoromethyl, dichloromethyl, trifluoromethyl, cyano, formyl, acetyl or phenyl; $R^5$ is hydrogen, methyl, amino or chloro; $R^2$ and $R^4$ are each independently selected from hydrogen, methyl, fluoro, chloro and bromo or, together with the carbon atom to which they are attached, form a cyclopropyl, cyclobutyl or cyclopentyl group; $R^6$ and $R^8$ are each independently selected from hydrogen, methyl, chloro and bromo; or, when $R^2$ and $R^4$ do not form part of a cycloalkyl group, $R^2$ and $R^6$, together with the carbon atoms to which they are attached, may form a cyclopentane or cyclohexane group; and $R^7$ is hydrogen, methyl, ethyl, trifluoromethyl, chlorodifluoromethyl, pentafluoroethyl, heptafluoropropyl or methoxy.

A more preferred group of compounds of formula (I) is that wherein $R^1$ is 2,6-dichloro-4-trifluoromethylphenyl, 2,6-dichloro-4-pentafluorothiophenyl or 3-chloro-5-trifluoromethylpyridin-2-yl; $R^3$ is cyano; $R^5$ is hydrogen or amino; $R^2$ and $R^4$ are the same and are hydrogen, chloro or bromo; $R^6$ and $R^8$ are hydrogen; and $R^7$ is hydrogen, trifluoromethyl or chlorodifluoromethyl.

Particularly preferred individual compounds of the invention include 3-cyano-4-(2,2-dibromocyclopropyl)-1-(2,6-dichloro-4-trifluoromethylphenyl)pyrazole;

(−)-3-cyano-4-(2,2-dibromocyclopropyl)-1-(2,6-dichloro-4-trifluoromethylphenyl)pyrazole;
3-cyano-1-(2,6-dichloro-4-trifluoromethylphenyl)-4-(1-trifluoromethylcyclopropyl)pyrazole;
3-cyano-4-(2,2-dibromocyclopropyl)-1-(2,6-dichloro-4-pentafluorothiophenyl)pyrazole;
3-cyano-4-(2,2-dichlorocyclopropyl)-1-(2,6-dichloro-4-pentafluorothiophenyl)pyrazole;
3-cyano-4-(2,2-dichlorocyclopropyl)-1-(2,6-dichloro-4-trifluoromethylphenyl)pyrazole;
4-(1-chlorodifluoromethylcyclopropyl)-3-cyano-1-(2,6-dichloro-4-trifluoromethylphenyl)pyrazole;
1-[(3-chloro-5-trifuoromethyl)pyridin-2-yl]-3-cyano-4-(2,2-dibromocyclopropyl)pyrazole;
5-amino-3-cyano-4-(2,2-dibromocyclopropyl)-1-(2,6-dichloro-4-trifluoromethylphenyl)pyrazole;
5-amino-3-cyano-4-(2,2-dibromocyclopropyl)-1-(2,6-dichloro-4-pentafluorothiophenyl)pyrazole;
5-amino-3-cyano-4-(2,2-dichlorocyclopropyl)-1-(2,6-dichloro-4-pentafluorothiophenyl)pyrazole; and
5-amino-3-cyano-1-(2,6-dichloro-4-trifluoromethylphenyl)-4-(1-trifluoromethylcyclopropyl)pyrazole.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below. It will be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard substituent or functional group interconversions and transformations within certain compounds of formula (I) will provide other compounds of formula (I). Examples are the deamination of a compound of formula (I) wherein $R^5$ is amino, the monodebromination of a compound of formula (I) wherein $R^2$ and $R^4$ are bromo, and the conversions of a compound of formula (I) wherein $R^3$ is cyano to a compound of formula (I) wherein $R^3$ is $C_1$ to $C_5$ alkanoyl, a compound of formula (I) wherein $R^3$ is $C_1$ to $C_4$ alkanoyl to a compound of formula (I) wherein $R^3$ is $C_1$ to $C_4$ alkyl substituted with hydroxy or with dihalo, and a compound of formula (I) wherein $R^3$ alkyl substituted with hydroxy to a compound of formula (I) wherein $R^3$ is $C_1$ to $C_4$ alkyl or $C_1$ to $C_4$ alkyl monosubstituted with halo.

Thus the following processes are illustrative of the general synthetic procedures which may be adopted in order to obtain the compounds of the invention.

1. A compound of formula (I) may be prepared by cyclopropanation of an alkene of formula (II):

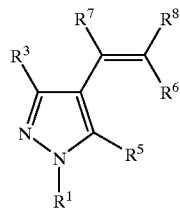

(II)

wherein $R^1$, $R^3$, $R^5$, $R^6$, $R^7$ and $R^8$ are as previously defined for formula (I). This may be achieved by in situ generation of the required carbenoid species, in the presence of (II), by an appropriate method. Such methods include treatment of chloroform or bromoform with base, preferably under phase transfer catalysis conditions, thermolysis of a suitable organometallic precursor such as an aryl trichloromethyl or tribromethyl mercury derivative, treatment with a diazoalkane in the presence of a transition metal catalyst and treatment with a diazoalkane in the absence of a transition metal catalyst followed by thermolysis of the intermediate pyrazoline.

For example in the first method, to prepare a compound of formula (I) wherein $R^2$ and $R^4$ are either both chloro or both bromo, chloroform or bromoform respectively is treated with a concentrated aqueous solution of an alkali metal hydroxide in the presence of (II) and a quaternary ammonium salt in a suitable solvent at from about room temperature to about the reflux temperature of the reaction medium. Preferably the reagents are sodium hydroxide and benzyltriethylammonium chloride respectively, while the solvent is preferably dichloromethane optionally in the presence of a small amount of ethanol.

In the second method for example, to prepare a compound of formula (I) wherein both $R^2$ and $R^4$ are either both chloro or both bromo, a mixture of (II) and either phenyltrichloromethylmercury or phenyltribromomethylmercury respectively is heated at from about 60° C. to about 75° C. in a suitable solvent, preferably toluene, xylene or a mixture thereof.

The third method is typified by treatment of (II) with an ethereal solution of diazomethane in the presence of palladium(II) acetate at about room temperature in a suitable solvent, preferably ether, which provides a compound of formula (I) wherein both $R^2$ and $R^4$ are hydrogen.

An alternative variation for preparing a compound of formula (I) wherein $R^2$ and $R^4$ are hydrogen is via the pyrazoline intermediate formed by employing the previous method in the absence of palladium(II) acetate. Subsequent thermolysis of the isolated pyrazoline in a suitable solvent, preferably xylene, at from about 135° C. to about 145° C. produces the required compound.

A compound of formula (II) may be obtained from a compound of formula (III):

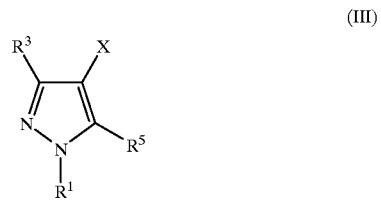

(III)

wherein X is bromo or iodo, and $R^1$, $R^3$ and $R^5$ are as previously defined for formula (II), with the proviso that $R^5$ is not bromo or iodo. Preferably X is iodo. The transformation may be achieved by a transition metal-catalysed cross-coupling reaction of (III) with an appropriate vinylation reagent in a suitable, optionally degassed, solvent. Preferably the transition metal is palladium and the vinylation reagent is an organotin derivative. For example, (III) is treated with tri-n-butyl(vinyl)tin in the presence of tetrakis(triphenylphosphine)-palladium(O) in dimethylformamide at from about room temperature to about 80° C. to afford a compound of formula (II) wherein $R^7$, $R^6$ and $R^8$ are hydrogen Alternatively, a compound of formula (II) wherein $R^5$ is hydrogen, $C_1$ to $C_4$ alkyl or halo may be obtained using conventional Wittig technology by reacting a compound of formula (V):

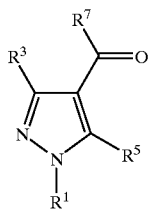

(V)

wherein $R^7$ is hydrogen or $C_1$ to $C_4$ alkyl optionally substituted with one or more halo, $R^5$ is hydrogen, $C_1$ to $C_4$ alkyl or halo, and $R^1$ and $R^3$ are as previously defined for formula (II), with the appropriate alkylphosphonium salt-derived phosphorus ylid.

For example treatment of a methyltriphenylphosphonium halide with a strong base in a suitable solvent, followed by the addition of (V), will produce a compound of formula (II) wherein both $R^6$ and $R^8$ are hydrogen. Preferably the base reagent is a solution of n-butyllithium in hexane, the solvent is ether or tetrahydrofuran and the reaction is conducted at from about room temperature to about 35° C.

For a compound of formula (II) wherein $R^7$ is $C_1$ to $C_4$ alkoxy, $R^6$ and $R^8$ are hydrogen, $R^5$ is hydrogen, $C_1$ to $C_4$ alkyl or halo, and $R^1$ and $R^3$ are as previously defined for formula (II), it is particularly convenient to use an alkene interconversion sequence whereby a compound of formula (II), wherein $R^7$, $R^6$ and $R^8$ are hydrogen, $R^5$ is hydrogen, $C_1$ to $C_4$ alkyl or halo, and $R^1$ and $R^3$ are as previously defined for formula (II), is treated with iodine in the appropriate $C_1$ to $C_4$ alkanol in the presence of a mercury(II) salt to provide the intermediate α-alkoxy-β-iodoethylpyrazole which, in turn, is dehydroiodinated with an appropriate base, optionally in a suitable solvent. For example, when $R^7$ is methoxy, the first step is conducted using mercuric oxide and iodine in methanol at about the reflux temperature of the reaction medium, whilst the second step may be effected using a tertiary amine base such as 1,8-diazabicyclo[5.4.0]undec-7-ene (DBU) in toluene at about room temperature.

A compound of formula (III) wherein $R^5$ is hydrogen or halo may be obtained from a compound of formula (III) wherein $R^5$ is amino by conventional deamination or deamination-halogenation procedures, respectively. When $R^5$ is hydrogen, a convenient procedure involves treatment of the amine with t-butyl nitrite in tetrahydrofuran as solvent at from about room temperature to 70° C. When $R^5$ is, for example, chloro, a solution of the amine in a suitable solvent such as acetonitrile may be treated with a solution of nitrosyl chloride in dichloromethane at about 0° C. followed by heating at the reflux temperature of the reaction mixture, In analogous fashion, a compound of formula (V) wherein $R^5$ is hydrogen or halo may be obtained from a compound of formula (V) wherein $R^5$ is amino The latter, in turn, is obtainable from a compound of formula (IV), wherein $R^5$ is amino and $R^1$ and $R^3$ are as previously defined for formula (III), by conventional acylation.

A compound of formula (III) wherein $R^5$ is $C_1$ to $C_4$ alkyl or amino may also be obtained from a compound of formula (IV):

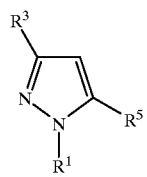

(IV)

wherein $R^5$ is $C_1$ to $C_4$ alkyl or amino and $R^1$ and $R^3$ are as previously defined for formula (III), by conventional bromination or iodination procedures. For example, when X is iodo, (IV) is treated with N-iodosuccinimide in a suitable solvent such as acetonitrile at from about room temperature to about 85° C.

A compound of formula (V) wherein $R^7$ is hydrogen may be conveniently obtained from a compound of formula (II) wherein $R^7$, $R^6$ and $R^8$ are hydrogen, $R^5$ is hydrogen, $C_1$ to $C_4$ alkyl or halo, and $R^1$ and $R^3$ are as previously defined for formula (II), by oxidation of the vinyl group by any of a variety of standard procedures. For examples, one such procedure involves treatment of the alkene with osmium tetroxide in the presence of 4-methylmorpholine-N-oxide in a suitable solvent, then subsequent treatment of the reaction mixture with sodium metaperiodate. Preferably the osmium tetroxide is introduced as a t-butanol solution, the reaction solvent is 90% aqueous acetone and the reaction is conducted at about room temperature.

Clearly, by analogy, this oxidation approach may also be used to prepare a compound of formula (V) wherein $R^7$ is $C_1$ to $C_4$ alkyl optionally substituted with one or more halo from the corresponding alkene. However, when $R^7$ is methyl, an alternative route to (V) is via hydration of a compound of formula (VI):

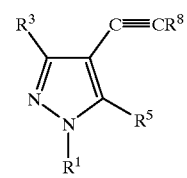

(VI)

wherein $R^8$ is hydrogen, and $R^1$, $R^3$ and $R^5$ are as previously defined for formula (V). Advantageously, this method can also be employed when $R^5$ is amino.

Thus treatment of the alkyne (VI) with acid in a suitable solvent at about room temperature furnishes the corresponding 4-acetylpyrazole derivative. Preferably, the acid is p-toluenesulphonic acid and the solvent is acetonitrile.

In turn, (VI) is obtainable from an appropriately protected precursor, e.g. a compound of formula (VI) wherein $R^8$ is trimethylsilyl. In such a case, deprotection can be effected using a mild base such as potassium carbonate in a suitable solvent such as methanol.

Conveniently, when $R^5$ is not bromo or iodo, the protected alkyne is accessible from a compound of formula (III) via a transition metal-catalysed cross coupling reaction with trimethylsilylacetylene in the presence of excess tertiary base in a suitable solvent. Preferably, the transition metal is palladium. Thus, for example, (III) is treated with trimethylsilylacetylene in the presence of bis(triphenylphosphine)-palladium(II) chloride, cuprous iodide and triethylamine in dimethylformamide at from about 45° C. to about 65° C.

A compound of formula (I) may also be prepared by an alternative cyclopropanation strategy, whereby the required carbenoid species is generated from a pyrazole-containing precursor in the presence of the appropriate alkene. One such precursor is represented by an arylsulphonylhydrazone derivative of a compound of formula (V), i.e. a compound of formula (VII):

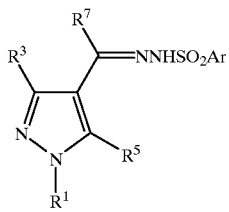

wherein Ar is phenyl or naphthyl either of which is optionally substituted with $C_1$–$C_4$ alkyl, $C_1$ to $C_4$ alkoxy or halo, and $R^1$, $R^3$, $R^5$ and $R^7$ are as previously defined for formula (V). Preferably, Ar is 4-methylphenyl (p-tolyl).

Thus (VII), in the form of an alkali metal salt derivative, preferably the lithium salt which is readily prepared from (VII) using a solution of n-butyllithium in hexane in a suitable solvent such as tetrahydrofuran at from about −78° C. to about room temperature, is thermally decomposed in the presence of a transition metal catalyst and an alkene of formula (VIII):

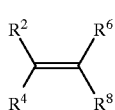

wherein $R^2$, $R^4$, $R^6$ and $R^8$ are as previously defined for formula (I), optionally in a suitable solvent such as dichloromethane and optionally under pressure. The reaction is normally conducted with a large excess of (VIII) at a temperature of from about room temperature to about 80° C. and a pressure of from about 101 kPa (14.7 psi) to about 2757 kPa (400 psi). Clearly, at elevated pressure, it will be necessary to use a pressure vessel (bomb), which is the preferred method for weakly reactive alkenes. Preferably, the transition metal catalyst is rhodium(II) in the form of a suitable salt, e.g. rhodium(II) acetate.

A typical procedure involves heating a mixture of the lithium salt of a compound of formula (VII), wherein Ar is 4-methylphenyl and $R^1$, $R^3$, $R^5$ and $R^7$ are as previously defined for formula (VII), (VIII) and rhodium(II) acetate dimer in anhydrous dichloromethane at from about 50° C. to about 70° C.

The intermediates of formula (IV) and (VII), if not subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The pharmaceutically, veterinarily and agriculturally acceptable acid addition salts of certain of the compounds of formula (I) may also be prepared in a conventional manner. For example, a solution of the free base is treated with the appropriate acid, either neat or in a suitable solvent, and the resulting salt isolated either by filtration or by evaporation under reduced pressure of the reaction solvent.

The compounds of the invention, i.e. those of formula (I), possess parasiticidal activity in humans, animals and plants. They are particularly useful in the treatment of ectoparasites.

Regarding the use of the compounds of the invention in humans, there is provided:

a pharmaceutical parasiticidal composition comprising a compound of formula (I), or a pharmaceutically acceptable salt thereof, or a pharmaceutically acceptable solvate of either entity, together with a pharmaceutically acceptable diluent or carrier, which may be adapted for topical administration; a compound of formula (I), or a pharmaceutically acceptable salt thereof, or a pharmaceutically acceptable solvate of either entity, or a pharmaceutical composition containing any of the foregoing, for use as a medicament; the use of a compound of formula (I), or a pharmaceutically acceptable salt thereof, or a pharmaceutically acceptable solvate of either entity, or a pharmaceutical composition containing any of the foregoing, for the manufacture of a medicament for the treatment of a parasitic infestation; and a method of treating a parasitic infestation in a human being which comprises treating said human being with an effective amount of a compound of formula (I), or a pharmaceutically acceptable salt thereof, or a pharmaceutically acceptable solvate of either entity, or a pharmaceutical composition containing any of the foregoing.

With respect to their use in non-human animals, the compounds may be administered alone or in a formulation appropriate to the specific use envisaged, the particular species of host animal being treated and the parasite involved. The methods by which the compounds may be administered include oral administration by capsule, bolus, tablet or drench, topical administration as a pour-on, spot-on, dip, spray, mousse, shampoo or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

As an alternative the compounds may be administered with the animal feedstuff and for this purpose a concentrated feed additive or premix may be prepared for mixing with the normal animal feed.

The compounds of the invention have utility in the control of arthropod pests. They may, in particular, be used in the fields of veterinary medicine, livestock husbandry and the maintenance of public health: against arthropods which are parasitic internally or externally upon vertebrates, particularly warm-blooded vertebrates, including man and domestic animals such as cattle, sheep, goats, equines, swine, poultry, dogs, cats and fish, for example Acarina including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata*), mites (e.g. Damalinia spp., *Dermnanyssus gailinae*, Sarcoptes spp. e.g. *Sarcoptes scabiei*, Psoroptes spp., Chorioptes spp., Demodex spp., Eutrombicula spp.); Diptera (e.g. Aedes spp., Anopheles spp., Muscidae spp. e.g. *Stomoxys calcitrans* and *Haematobia irritans*, Hypoderma spp., Gastrophilus spp., Simulium spp.), Hemiptera (e.g. Triatoma spp.); Phthiraptera (e.g. Damalinia spp., Linognathus spp.); Siphonaptera (e.g. Ctenocephalides spp.); Dictyoptera (e.g. Periplaneta spp., Blatella spp.) and Hymenoptera (e.g. *Monomorium pharaonis*); in the protection of stored products, for example cereals including grain and flour, groundnuts, animal foodstuffs, timber and household goods, e.g. carpets and textiles, against attack by arthropods, more especially beetles including weevils, moths and mites, for example Ephestia spp. (flour moths), Anthrenus spp. (carpet beetles), Tribolium spp. (flour beetles), Sitophilus spp. (grain weevils) and Acarus spp. (mites); in the control of cockroaches, ants and termites and similar arthropod pests in infested domestic and industrial premises; in the control of mosquito larvae in waterways, wells, reservoirs or other running or standing water; in the treatment of foundations, structure and soil for the prevention of attack on buildings by termites, for example Reticulitermes spp., Heterotermes spp., Coptotermes spp.; in agriculture against adults, larvae and eggs of Lepidoptera (butterflies and moths) e.g. Heliothis spp. such as *Heliothis virescens* (tobacco budworm), *Heliothis armioera* and *Heliothis zea*, Spodoptera spp. such as *S. exempta, S. littoralis* (Egyptian cotton worm), *S. eridania* (southern army worm), *Mamestra configurata* (bertha army worm), Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphyqma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond black moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Melioethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp., Nymenoptera e.g. Athalia spp. and Cephus spp. (saw flies), Atta spp. (leaf cutting ants), Diptera e.g. Hylemyia spp. (root flies), Atherigona spp. and Chlorops spp. (shoot flies), Phytomyza spp. (leaf miners), Ceratitis spp. (fruit flies), Thysanoptera such as *Thrips tabaci*, Orthoptera such as Locusta and Schistocerca spp. (locusts) and crickets e.g. Gryllus spp. and Acheta spp., Collembola e.g. Sminthurus spp. and Onychiurus spp. (springtails), Isoptera e.g. Odontotermes spp. (termites), Dermaptera e.g. Forficula spp. (earwigs) and also against other arthropods of agricultural significance such as Acari (mites) e.g. Tetranychus spp., Panonychus spp. and Bryobia spp. (spider (mites), Eriophyes spp. (gall mites), Polyphacotarsonemus spp., Blaniulus spp. (millipedes), Scutigerella spp. (symphilids), Oniscus spp. (woodlice) and Triops spp. (crustacea).

The compounds of the invention also have utility in the control of arthropod pests of plants. The active compound is generally applied to the locus at which the arthropod infestation is to be controlled at a rate of about 0.005 kg to about 25 kg of active compound per hectare (ha) of locus treated, preferably 0.02 to 2 kg/ha. Under ideal conditions, depending on the pest to be controlled, the lower rate may offer adequate protection. On the other hand. adverse weather conditions and other factors may require that the active ingredient be used in higher proportions. For foliar application, a rate of 0.01 to 1 kg/ha may be used.

When the pest is soil-borne, the formulation containing the active compound is distributed evenly over the area to be treated in any convenient manner. Application may be made, if desired, to the field or crop-growing area generally, or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place, or after sprouting.

The compounds of the invention are of value in controlling pests which feed on parts of the plant remote from the point of application, e.g. leaf feeding insects may be killed by applying the subject compounds to roots. In addition, the compounds may reduce attacks on the plant by means of antifeeding or repellent effects.

The compounds of the invention are of particular value in the protection of field, forage, plantation, glasshouse, orchard and vineyard crops, or ornamentals, and of plantation and forest trees, for example cereals (such as maize, wheat, rice, sorghum), cotton, tobacco, vegetables and salads (such as bean, cole crops, curcurbit, lettuce, onion, tomato and pepper), field crops (such as potato, sugar beet, ground nut, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olive and walnut), vineyards, ornamental plants, flowers and shrubs under glass, in gardens and in parks, and forest trees (both deciduous and evergreen) in forests, plantations and nurseries.

They are also valuable in the protection of timber (standing, felled, converted, stored or structural) from attack by sawflies (e.g. Urocerus), beetles (e.g. scolytids, platypodids, lyctids, bostrychids, cerambycids, anobiids) or termites (e.g. Reticulitermes spp., Heterotermes spp., Coptotermes spp.).

Moreover, they have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack, as are meat and fish from beetle, mite and fly attack.

The compounds of the invention are of value in the control or arthropods which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

Therefore, according to a further aspect of the invention, there is provided a veterinary or agricultural formulation comprising a compound of formula (I), or a veterinarily or agriculturally acceptable salt thereof, or a veterinarily or agriculturally acceptable solvate of either entity, together with a veterinarity or agriculturally acceptable diluent or carrier. Preferably, the formulation is adapted for topical administration.

The invention further provides a compound of formula (I), or a veterinarily or agriculturally acceptable salt thereof, or a veterinarily or agriculturally acceptable solvate of either entity, or a veterinarily or agriculturally acceptable formulation containing any of the foregoing, for use as a parasiticide.

It also provides a method of treating a parasitic infestation at a locus, which comprises treatment of the locus with an effective amount of a compound of formula (I), or a veterinarily or agriculturally acceptable salt thereof, or a veterinarily or agriculturally acceptable solvate of either entity, or a veterinarily or agriculturally acceptable formulation containing any of the foregoing.

Preferably, the locus is the skin or fur of an animal, or a plant surface, or the soil around the plant to be treated.

It is to be appreciated that reference to treatment includes prophylaxis as well as the alleviation and/or cure of established symptoms of a parasitic infection.

Test for Insecticidal Activity

Adult flies (Stomoxys calcitrans) are collected and anaesthetized using $CO_2$. An acetone solution (1 μl) containing the test compound is applied directly to the thorax of each fly and then the flies are placed carefully into a 50 ml tube covered with damp gauze to recover from the $CO_2$. Negative controls have acetone (1 μl) dispensed onto them. Mortality is assessed 24 hours after dosing. Table 1 illustrates the in vitro activity of a selection of the compounds of the invention against adult Stomoxys calcitrans. Dosages required to produce 100% mortality are given in the final column as μg/fly.

TABLE 1

| EXAMPLE NO. | μg/FLY |
|---|---|
| 3A | 0.05 |
| 7 | 0.05 |
| 19 | 0.05 |
| 27 | 0.05 |
| 47 | 0.05 |

Test for Acaricidal Activity

A dose of 10 μg/cm² is created by evenly pipetting 0.5 ml of a 1 mg/ml solution of the test compound in a suitable solvent such as acetone or ethanol onto a Whatman No. 1 (Trade Mark) filter paper cut to a size of 8×6.25 cm. When dry, the paper is folded in half, sealed on two sides using a crimping device and placed in a Kilner jar containing a cotton wool pad dampened with water. The jar is then sealed and placed at 25° C. for 24 hours. Next, approximately 50 Boophilus microplus larvae are introduced into the treated paper envelope which is then crimped along the third side to effect a complete seal. The paper envelope is returned to the Kilner jar, which is sealed and placed at 25° C. for a further 48 hours. The papers are then removed and mortality assessed. Negative controls are provided by treating an appropriately cut filter paper with 0.5 ml of solvent only and following the same procedure. Activity at other doses is obtained by varying the concentration of the test solution.

Table 2 illustrates the in vitro activity of a selection of the compounds of the invention against Boophilus microplus larvae. Dosages required to produce 100% mortality are given in the final column as μg/cm².

TABLE 2

| EXAMPLE NO. | μg/cm² |
|---|---|
| 3A | 0.50 |
| 7 | 0.50 |
| 19 | 0.50 |
| 47 | 1.00 |

The syntheses of the compounds of the invention and of the intermediates or use therein are illustrated by the following Examples and Preparations.

Melting points were determined using a Gallenkamp melting point apparatus and are uncorrected.

Nuclear magnetic resonance (NMR) spectral data were obtained using a Bruker AC300 or AM300 spectrometer, the observed chemical shifts (a) being consistent with the proposed structures.

Mass spectral (MS) data were obtained on a Finnigan Mat. TSQ 7000 or a Fisons Instruments Trio 1000 spectrometer. The calculated and observed ions quoted refer to the isotopic composition of lowest mass.

HPLC means high performance liquid chromatography.

Room temperature means 20 to 25° C.

EXAMPLE 1

5-Amino-3-cyano-4-(2,2-dibromocycloproyl)-1-(2,6-dichloro-4-trifluoromethylphenyl)pyrazole A vigorously stirred mixture of the title compound of Preparation 2 (1.0 g), bromoform (13 ml), benzyltriethethylammonium chloride (0.075 g), 60% aqueous sodium hydroxide solution (2 ml), dichloromethane (12 ml) and ethanol (0.5 ml) was heated under reflux for 10 days, then allowed to cool and diluted with water. The separated organic phase was applied to a column of silica gel (10 g) and elution with dichloromethane effected. The crude product obtained from the appropriate fractions was purified by reverse phase HPLC on C18 silica, using acetonitrile:water:methanol (50:40:10) as eluant, to give the title compound as an off-white solid, m.p. 178–179° C. δ(CDCl$_3$):2.28 (d,2H),2.61 (t,1H), 3.80 (br.s,2H), 7.8 (s,2H). MS (thermospray): M/Z [M+H] 516.4; $C_{14}H_7Br_2Cl_2F_3N_4$+H requires 516.84.

EXAMPLE 2

3-Cyano-4-(2,2-dibromocyclopropyl)-1-(2,6-dichloro-4-trifluoromethylphenyl)pyrazole Ethanol (0.1 ml) and a solution of sodium hydroxide (0.29 g) in water (0.5 ml) were added to a stirred solution of the title compound of Preparation 4 (0.6 g) and bromoform (1.83 g) in dichloromethane (2 ml), followed by benzyltriethylammonium chloride (0.1 g). The reaction mixture was stirred, successively, at room temperature for 18 hours, at 50° C. for 5 hours, at room temperature for 48 hours, at 50° C. for 4 hours and at room temperature for 18 hours, then partitioned between dichloromethane (100 ml) and water (100 ml). The organic phase was separated, dried (MgSO$_4$) and evaporated under reduced pressure to provide an oil which was purified by column chromatography on silica gel (10 g), using hexane dichloromethane (3:7) as eluant, followed by crystallisation of the required material from hexane.

The title compound was thus obtained as a white solid, m.p. 121–123° C. δ(CDCl$_3$): 2.02 (t,1H), 2.34 (dd,1H), 2.88 (dd,1H), 7.53 (s,1H), 7.78 (s,2H). MS(thermospray): M/Z [M+NH$_4$] 518.9; $C_{14}H5Br_2Cl_2F_3N_3$+NH$_4$ requires 518.86

EXAMPLES 3A and 3B

A. (−)-3-Cyano-4-(2,2-dibromocyclopropyl)-1-(2,6-dichloro-4-trifluoromethylphenyl)pyrazole and
B. (+)-3-Cyano-4-(2,2-dibromocyclopropyl)-1-(2,6-dichloro-4-trifluoromethylphenyl)pyrazole The title compound of Example 2 (28.5 mg) was resolved by chiral HPLC using a Chiralpak (Trade Mark) AD column (25 cm×2 cm), a mixture of hexane: propan-2-ol (93:7) as eluant and an elution rate of 9 ml/minute.

The (−)-enantiomer (A) eluted first and was obtained as a white crystalline solid, m.p. 132.5–135° C.

$[\alpha]_D^{25}$ −42.54° (c=1.5 mg/ml, methanol).

The (+)-enantiomer (B) eluted second and was obtained as a white crystalline solid, m.p. 132.5–134° C.

$[(\alpha]_D^{25}$ +44.02° (c=3.5 mg/ml, methanol).

It was determined by X-ray crystallographic analysis that this latter enantiomer possesses the R-configuration.

EXAMPLE 4

3-Cyano-4-(2,2-dichlorocyclopropyl)-1-(2,6-dichloro-4-trifluoromethylphenyl)pyrazole Benzyltriethylammonium chloride (0.01 g) and ethanol (0.015 ml) were added to a stirred solution of the title compound of Preparation 4 (0.46 g) in chloroform (0.66 ml). 50% Aqueous sodium hydroxide solution (0.25 ml) was then added and the reaction mixture stirred at 60° C. for 1 month. The resulting mixture was partitioned between dichloromethane and water, then the organic phase separated, dried (MgSO$_4$) and evaporated under reduced pressure. The brown gum thus obtained was purified by column chromatography on silica gel (10 g), using dichloromethane as eluant, followed by reverse phase HPLC on C18 silica, using acetonitrile:water:methanol (50:40:10) as eluant. Crystallisation of the required material from hexane furnished the title compound as colourless plates, m.p. 123–126 C. 67 (CDCl$_3$):1.84 (t,1 H), 2.20 (dd,1H), 2.85 (dd,1H), 7.53 (s,1H), 7.78 (s,2H). MS (thermospray): M/Z [M+NH$_4$] 430.6;$C_{14}H_6Cl_4F_3N_3$+NH$_4$ requires 430.96.

EXAMPLE 5

5-Amino-3-cyano-4-(2,2-dibromocyclopropyl)-1-(2,6-dichloro-4-pentafluorothiophenyl)pyrazole Bromoform (6.4 ml), followed by ethanol (0.1 ml) and a solution of sodium hydroxide (0.29 g) in water (0.5 ml), were added to a stirred solution of the title compound of Preparation 6 (0.35 g) in dichloromethane (2 ml). Benzyltriethylammonium chloride (0.1 g) was next added and the reaction mixture stirred at 50° C. for 13 days, then allowed to cool. The resulting mixture was evaporated under reduced pressure and the residue partitioned between dichloromethane and water. The organic phase was separated and combined with ethyl acetate extracts of the aqueous phase, then the combined organic solutions were washed with brine, dried and evaporated under reduced pressure. The residue was purified by column chromatography on silica gel, using dichloromethane as eluant, followed by reverse phase HPLC on C18 silica gel, using acetonitrile:water:methanol (60:30:10) as eluant, to afford the title compound as a white solid, m.p. 178–180° C. δ(CDCl$_3$): 2.29 (d,2H), 2.60 (t,1H), 3.89 (br.s,2H), 7.93 (d.2H). MS (thermospray): M/Z [M+H]574.7; $C_{13}H_7Br_2Cl_2F_5N_4S$+H requires 574.81.

EXAMPLE 6

3-Cyano-4-(2,2-dibromocyclopropyl)-1-(2,6-dichloro-4-pentafluorothiophenyl)pyrazole Obtained as a white foam from the title compound of Preparation 8 by analogy with Example 5, but using hexane:dichloromethane (1:1) as eluant in the initial column chromatography purification step. δ(CDCl$_3$): 2.01 (t,1H), 2.34 (dd,1H), 2.88 (dd,1H), 7.54 (s,1H), 7.91(d,2H). MS (thermospray): M/Z [M+N H$_4$]576.8;$C_{13}H_6Br_2Cl_2F_5N_3S$+NH$_4$ requires 576.83.

EXAMPLE 7

3-Cyano-4-cyclopropyl-1-(2,6-dichloro-4-trifluoromethylphenyl)pyrazole

A 0.2 M solution of diazomethane in ether (25 ml) was added over 25 minutes to a stirred solution of the title compound of Preparation 4 (0.3329) and palladium(II) acetate (0.01 g) in ether (10 ml) and the mixture stirred at room temperature for 18 hours. The reaction mixture was treated with additional quantities of the ethereal diazomethane solution (25 ml) and palladium(II) acetate (0.01 g), stirred for 24 hours, further treated with the ethereal diazomethane solution (50 ml) and palladium(II) acetate (0.01 g), stirred for 24 hours more, then evaporated under reduced pressure. The residue was purified by column chromatography on silica gel (5 g), using dichloromethane as eluant, followed by reverse phase HPLC on C18 silica, using acetonitrile:water: methanol (50:45:5) as eluant, to give the title compound as a white solid, m.p. 124° C. δ(CDCl$_3$): 0.77 (m,2H), 1.07 (m,2H), 1.89 (m,1H), 7.29 (s,1H) 7.74 (s,2H). MS (thermospray): M/Z [M+NH$_4$] 362.8; $C_{14}H_8Cl_2F_3N_3$+NH$_4$ requires 363.04.

EXAMPLE 8

3-Cyano-4-(2,2-dibromo-3,3-dimethylcyclopropyl)-1-(2,6-dichloro-4-trifluoromethylphenyl)pyrazole A solution of the title compound of Preparation 10 (0.15 g) and phenyltribromomethylmercury (0.44 g) in toluene (2 ml) was heated at 70° C. for 5 hours, allowed to cool and evaporated under reduced pressure. The residue was purified by reverse phase HPLC on C18 silica, using acetonitrile:water: methanol (60:30:10) as eluant, to yield the title compound as an off-white solid, m.p. 146–148° C. δ(CDCl$_3$): 1.31 (s,3H), 1.70 (s,3H), 2.52 (s,1H), 7.78 (s,2H), 7.79 (s,1H). MS (thermospray): M/Z [M+NH$_4$] 546.7; $C_{16}H_{10}Br_2Cl_2F_3N_3$+NH$_4$ requires 546.89

EXAMPLE 9

3-Cyano-4-(2,2-dibromo-1-methylcyclopropyl)-1-(2,6-dichloro-4-trifluoromethylphenyl)pyrazole Obtained from the title compound of Preparation 15 by analogy with Example 8, but employing a reaction time of 4 hours followed by filtration of the reaction mixture and an initial column chromatography on silica gel purification step using hexane:dichloromethane (1:1) as eluant, as a white solid, m.p. 133–134 °C. δ(CDCl$_3$): 1.83 (s,3H), 1.92 (d,1H), 2.28 (d,1H), 7.59 (s,1H), 7.78 (s,2H). MS (thermospray): M/Z [M+NH$_4$] 533.0; $C_{15}H_8Br_2Cl_2F_3N_3$+NH$_4$ requires 532.88.

EXAMPLE 10

3-Cyano-1-(2,6-dichloro-4-trifluoromethylphenyl)-4-(1-methylcyclopropyl)-pyrazole A 0.007 M solution of diazomethane in ether (20 ml) was added in two equal portions to a stirred solution of the title compound of Preparation 15 (0.346 g) and palladium(II) acetate (0.1 g) in ether (10 ml) and the mixture stirred at room temperature for 48 hours, then filtered. The reaction mixture was treated with additional quantities of the ethereal diazomethane solution (20 ml) and palladium(II) acetate (0.1 g), stirred for 24 hours and filtered, then this cycle repeated. The reaction mixture was further treated with the ethereal diazomethane solution (20 ml) and palladium(II) acetate (0.1 g), stirred for 5 days, filtered and evaporated under reduced pressure. Crystallisation of the residue from cyclohexane provided the title compound as a yellow solid, m.p. 138–139° C. δ(CDCl$_3$): 0.86 (m,2H), 1.04 (m,2H), 1.50 (s,3H), 7.41 (s,1H), 7.74 (s,2H). MS (thermospray): M/Z [M+H] 359.8; $C_{15}H_{10}Cl_2F_3N_3$+H requires 360.03.

EXAMPLE 11

3-Cyano-4-(2,2-dibromo-1-methoxycyclopropyl)-1-(2,6-dichloro-4-trifluoromethylphenyl)pyrazole A solution of the title compound of Preparation 17 (0.4 g) and phenyltribromomethylmercury (0.76 g) in toluene (1 ml) was heated at 60° C. for 4 hours, allowed to cool and evaporated under reduced pressure. The residue was purified by column chromatography on silica gel, using hexane:dichloro-methane (1:1) as eluant, to furnish the title compound as a white solid, m.p. 117–118° C. δ(CDCl$_3$): 2.22 (d,1H), 2.40 (d,1H), 3.43 (s,3H), 7.80 (s,2H), 7.84 (s,1H). MS (thermospray): M/Z [M+H] 532.1; $C_{15}H_8Br_2Cl_2F_3N_3O$+H requires 531.84.

EXAMPLE 12

3-Cyano-1-(2,6-dichloro-4-triflucromethylphenyl)-4-(2,2,3,3-tetramethylcyclopropyl)pyrazole A solution of the title compound of Preparation 18 (0.04 g), 2,3-dimethylbut-2-ene (1.08 ml) and rhodium(II) acetate dimer (0.001 g) in dichloromethane (0.3 ml) was heated to 70° C. over 30 minutes and kept at this temperature for a further 30 minutes. Dichloromethane (0.3 ml) was added to the reaction mixture which was then heated for a further 1 hour, allowed to cool and partitioned between dichloromethane (5 ml) and water (2 ml). The organic phase was separated, dried (Na$_2$SO$_4$) and evaporated under reduced pressure, then the residue purified by column chromatography on silica gel (1g), using dichloromethane as eluant, to afford the title compound as a white crystalline solid, m.p. 158–159 ° C. δ(CDCl$_3$): 1.05 (s,6H), 1.33 (s,6H), 1.55 (s,1H), 7.38 (s,1H), 7.75 (s,2H). MS (thermospray): M/Z [M+NH$_4$] 419.6; $C_{18}H_{16}Cl_2F_3N_3$+NH$_4$ requires 419.1.

EXAMPLE 13

3-Cyano-4-(t-2,t-3-dichloro-r-1-cyclopropyl)-1-(2,6-dichloro-4-trifluoromethylphenyl)pyrazole A solution of the title compound of Preparation 18 (0.2549, cis-1,2-dichloroethylene (7.0 g) and rhodium(II) acetate dimer (0.045 g) in anhydrous dichloromethane (7.5 ml) was heated at 60° C. for 4.5 hours and then allowed to stand at room temperature for 18 hours. The resulting mixture was purified by column chromatography on silica gel (50 g), using dichloromethane as eluant, to give the title compound as a white solid, m.p. 138–139° C. δ(CDCl$_3$): 2.80 (t,1H), 3.80 (d,2H), 7.75 (s,1H), 7.80 (s,2H). MS (thermospray): M/Z [M+NH$_4$9 431.3: $C_{14}H_6Cl_4F_3N_3$+NH$_4$ requires 430.96.

EXAMPLE 14

3-Cyano-4-(t-2,t-3-dibromo-r-1-cyclopropyl)-1-(2,-dichloro-4-trifluoromethylphenyl)pyrazole Obtained from the title compound of Preparation 18 and 1,2-dibromoethylene by analogy with Example 13, but heating the reaction mixture at 55° C. for 4 hours and ultimately freeze-drying the residue obtained after the chromatographic purification step from t-butanol, as a pale yellow solid, m.p. 106–108° C. δ(CDCl$_3$): 2.76 (t,1H), 3.80 (d,2H), 7.78 (s,2H), 7.80 (s,1 H), MS (thermospray): M/Z [M+H] 502.0; $Cl_{14}H_6Br_2Cl_4F_3N_3$+H requires 501.83.

EXAMPLE 15

3-Cyano-4-(bicyclo[3,1,0]hexan-6-yl)-1-(2,6-dichloro-4-trifluoro-methylphenyl)pyrazole Obtained from the title compound of Preparation 18 and cyclopentene by analogy with Example 13, but heating the reaction mixture at 55° C. for 4 hours, as a white solid, m.p. 105–106° C. δ(CDCl$_3$): 1.41–2.06 (m,9H), 7.47 (s,1H), 7.75 (s,2H). MS (thermospray): M/Z [M+NH$_4$] 403.4; $C_{17}H_{12}Cl_2F_3N_3$+NH$_4$ requires 403.07.

EXAMPLE 16

3-Cyano-4-(bicyclo[4,1,0]heptan-7-yl)-1-(2,6-dichloro-4-trifluoromethylphenyl)pyrazole Obtained from the title compound of Preparation 18 and cyclohexene by analogy with Example 15 as a white solid, m.p. 113–114° C. δ(CDCl$_3$): 0.87 (m,2H), 1.21 (m,2H), 1.46 (m,2H), 1.59 (m,2H), 1.78 (t,1H), 2.04 (m,2H), 7.52 (s,1H), 7.77 (s,2H). MS (thermospray): M/Z [M+NH$_4$] 417.0; $C_{18}H_{14}Cl_2F_3N_3$+NH$_4$ requires 417.09.

EXAMPLE 17

3-Cyano-1-(2,6-dichloro-4-trifluoromethylphenyl)-4-(2,2-dimethyl-cyclopropyl)pyrazole A solution of the title compound of Preparation 18 (0.507 g) and rhodium(II) acetate dimer (0.045 g) in anhydrous dichloromethane (7 ml) was placed in a glass-lined bomb (50 ml capacity) which was then flushed twice with nitrogen. The reaction vessel was charged with 2-methylpropene and the reaction mixture heated at 55° C. for 2 hours, then allowed to stand at room temperature for 18 hours. The resulting mixture was purified by column chromatography on silica gel (50 g), using dichloromethane as eluant, to yield the title compound as a very pale yellow solid, m.p. 122–123° C. δ($CDCl_3$): 0.70 (m,1H), 0.96 (s,3H), 1.00 (m,1H), 1.26 (s,3H), 1.74 (m,1H), 7.25 (s,1H), 7.76 (s,2H). MS (thermospray): M/Z [M+$NH_4$] 390.7; $C_{16}H_{12}Cl_2F_3N_3$+$NH_4$ requires 391.07.

EXAMPLE 18

3-Cyano-1-(2,6-dichloro-4-trifluoromethylphenyl)-4-(spiro[2.4]heptan-1-yl)prazole Obtained from the title compound of Preparation 18 and methylenecyclopentane by analogy with Example 15, but heating the reaction mixture for only 3 hours, as a pale yellow solid, m.p. 117–118° C. δ($CDCl_3$): 0.88 (t,1H), 1.22 (dd,1H), 1.37 (m,2H), 1.74 (m,6H), 1.92 (dd,1H), 7.27 (s,1H), 7.74 (s,2H). MS (thermospray): M/Z [M+$NH_4$] 417.1; $C_{18}H_{14}Cl_2F_3N_3$+$NH_4$ requires 417.09.

EXAMPLE 19

3-Cyano-1-(2,6-dichloro-4-trifluoromethylphenyl)-4-(2,2-difluorocyclopropyl)pyrazole Obtained from the title compound of Preparation 18 and 1,1-difluoroethylene by analogy with Example 17, but heating the reaction mixture at 50° C. and 2068 kPa (300 psi) for 24 hours. The product was further purified by repeated reverse phase HPLC on C18 silica, using acetonitrile:water (55:45) as eluant, to provide the title compound as a white amorphous solid. δ($CDCl_3$): 1.58 (m,1H), 2.16 (m,1H), 2.76 (m,1H), 7.50 (s,1H), 7.78 (s,2H). MS (APCl): M/Z [M+H] 382.0; $C_{14}H_6Cl_2F_5N_3$+H requires 381.99.

EXAMPLE 20

3-Cyano-1-(2,6-dichloro-4-trifluoromethylphenyl)-4-(spiro[2,3]hexan-1-yl)pyrazole Obtained from the title compound of Preparation 18 and methylenecyclobutane by analogy with Example 15, but heating the reaction mixture under reflux for 4 hours and then omitting the subsequent over-night standing at room temperature, to furnish the title compound as a white solid, m.p. 108–110° C. δ($CDCl_3$): 0.79 (m,1H), 1.24 (m,1H), 1.86–2.39 (m,7H), 7.08 (s,1H), 7.76 (s,2H). MS (thermospray): M/Z [M+$NH_4$] 403.0; $C_{17}H_{12}Cl_2F_3N_3$+$NH_4$ requires 403.07.

EXAMPLE 21

3-Cyano-1-(2,6-dichloro-4-trifluoromethylphenyl)-4-(spiro[2,2]pentan-2-yl)pyrazole A stirred solution of the title compound of Preparation 18 (0.507 g), methylenecyctopropane (5 ml) and rhodium(II) acetate dimer (0.045 g) in anhydrous dichloromethane (7 ml) was heated at 55° C. for 24 hours in a sealed, thick-walled, glass container and then allowed to cool. The resulting mixture was purified as in Example 13 to afford the title compound as a white solid, m.p. 108–110° C. δ($CDCl_3$): 0.81 (m,1H), 0.91 (m,1H), 0.99–1.18 (m,3H), 1.66 (dd,1H), 2.21 (dd,1H), 7.29 (s,1H), 7.74 (s,2H). MS (thermospray): M/Z [M+$NH_4$] 389.1; $C_{16}H_{10}Cl_2F_3N_3$+$NH_4$ requires 389.05.

EXAMPLE 22

4-(2,2-Dibromocyclopropyl)-1-(2,6-dichloro-4-trifluoromethylphenyl)-3-methylpyrazole Bromoform (1.08 ml), followed by a solution of sodium hydroxide (0.495 g) in water (1 ml) and ethanol (0.1 ml), were added to a stirred solution of the title compound of Preparation 22 (0.993 g) in dichloromethane (4 ml). Benzyltriethylammonium chloride (0.222 g) was next added and the reaction mixture heated at 50° C. for 6 days. The same quantities of bromoform, aqueous sodium hydroxide solution and ethanol were again added and stirring at 50° C. continued for 5 days. The cool reaction mixture was partitioned between ether and water, then the aqueous phase separated and extracted with ether (×2). The combined organic solutions were dried ($Na_2SO_4$) and evaporated under reduced pressure, then the residue purified by column chromatography on silica gel, using hexane:dichloromethane (3:2) as eluant, followed by trituration with cold hexane, to give the title compound as an off-white solid, m.p. 66.8–68.2° C. δ($CDCl_3$): 1.87 (t,1H), 2.19 (dd,1H), 2.47 (s,3H), 2.64 (dd,1H), 7.22 (s,1H), 7.80 (s,2H). MS (thermospray): M/Z [M+H] 491.0; $C_{14}H_9Br_2Cl_2F_3N_2$+H requires 490.85.

EXAMPLE 23

4-(2,2-Dibromocyclopropyl)-1-(2,6-dichloro-4-trifluoromethylphenyl)-3,5-dimethylpyrazole Bromoform (1.1 g), followed by a solution of sodium hydroxide (0.175 g) in water (0.5 ml) and ethanol (0.1 ml), were added to a stirred solution of the title compound of Preparation 25 (0.368 g) in dichloromethane (2 ml). Benzyltriethylammonium chloride (0.1 g) was next added and the reaction mixture heated under reflux for 4 days. The same quantities of bromoform, aqueous sodium hydroxide solution and ethanol were again added and stirring under reflux continued for 9 days. The cool reaction mixture was diluted with dichloromethane (20 ml), then this mixture washed successively with water (3×15 ml) and brine (10 ml), dried ($MgSO_4$) and evaporated under pressure. The residue was purified by column chromatography on silica gel (30 g) using hexane and then hexane:ether:dichloromethane (8:1:1) as eluants, followed by reverse phase HPLC on C18 silica using acetonitrile:water:methanol (60:30:10) as eluant, to yield the title compound as an oil. δ($CDCl_3$): 1.93 (t,1H), 2.10 (s,3H), 2.19 (dd,1H), 2.36 (s,3H), 2.60 (dd,1H), 7.73 (s,2H). MS (thermospray,): M/Z [M+H] 504.9; $C_{15}H_{11}Br_2Cl_2F_3N_2$+H requires 504.87.

EXAMPLE 24

4-(2,2-Dibromocyclopropyl)-3-meth-1-(2,4,6-trichlorophenyl)pyrazole

A solution of sodium hydroxide (0.64 g) in water (1 ml) and ethanol (0.1 ml) were added to a stirred solution of the title compound of Preparation 28 (1.0 g), bromoform (2 ml) and benzyltriethylammonium chloride (0.04 g) in dichloromethane (2 ml) and the reaction mixture heated under reflux for 16 hours, then allowed to cool. The resulting mixture was partitioned between dichloromethane and water, then the organic phase separated, washed successively with water and brine, dried ($Na_2SO_4$) and evaporated under reduced pressure. The residue was purified by column chromatography on silica gel, using hexane:ethyl acetate (50:1) as eluant, to provide a yellow oil which was further purified in similar fashion, using hexane:ethyl acetate (19:1) as eluant, followed by trituration with propan-2-ol, to furnish the title compound as a yellow solid, m.p. 84–86° C. δ(CDCl$_3$): 1.79 (t,1H), 2.19 (dd,1H), 2.44 (s,3H), 2.63 (dd,1H), 7.18 (s,1H), 7.44 (s,2H). MS (thermospray): M/Z [M+H] 456.8; C$_{13}$H$_9$Br$_2$Cl$_3$N$_2$+H requires 456.83.

EXAMPLE 25

4-(2,2-Dichlorocyclopropyl)-3-methyl-1-(2,4,6-trichlorophenyl)pyrazole

A 50% aqueous solution of sodium hydroxide (2 ml) was added to a stirred solution of the title compound of Preparation 28 (1.0 g), chloroform (7 ml) and benzyltriethylammonium chloride (0.08 g) in a mixture of ethanol (0.2 ml) and dichloromethane (2 ml), then the reaction mixture heated under reflux for 16 hours. Further quantities of chloroform (3 ml), benzyltriethylammonium chloride (0.04 g) and the sodium hydroxide solution (1 ml) were added, then this mixture stirred under reflux for 16 hours, allowed to cool and partitioned between dichloromethane and water. The organic phase was separated, washed successively with water and brine, dried (Na$_2$SO$_4$) and evaporated under reduced pressure. The residue was purified by column chromatography on silica gel, using hexane:ethyl acetate (19:1) as eluant, to afford a yellow oil which was further purified by reverse phase HPLC on C18 silica, using acetonitrile:water:methanol (60:30:10) as eluant, to give the title compound as a colourless oil. δ(CDCl$_3$): 1.61 (t,1H), 2.02 (dd,1H), 2.42 (s,3H), 2.63 (dd,1H), 7.20 (s,1H), 7.47 (s,2H). MS (thermospray): M/Z [M+H] 368.8; C$_{13}$H$_9$ Cl$_5$N$_2$+H requires 368.93.

EXAMPLES 26A AND 26B

A. 4-(c-2-Bromo-r-1-cyclopropyl)-3-cyano-1-(2.6-dichloro-4-trifluoromethylphenyl)pyrazole and
B. 4-(t-2-Bromo-r-1-cyclopropyl)-3-cyano-1-(2.6-dichloro-4-trifluoromethylphenyl)pyrazole Tri-n-butyltin hydride (0.9 g) was added dropwise, via syringe, to a stirred solution of the title compound of Example 2 (0.504 g ) in toluene (10 ml) at −10° C. The reaction mixture was allowed to warm to room temperature, stirred for 5 hours, kept at −20° C. for 3 days. allowed to warm to room temperature again and then treated with more tri-n-butyltin hydride (0.9 g). This mixture was stirred for a further 24 hours, treated with water and then, after 30 minutes, the aqueous phase was separated and extracted with dichloromethane. The combined organic phases were dried and evaporated under reduced pressure to provide a brown oil which was purified by column chromatography on silica gel, using hexane:dichloromethane (4:1) and then dichloromethane as eluants, followed by crystallisation of the required product from diprop-2-yl ether, to yield isomer A as a greyish-white solid, m.p. 120.5–121° C. δ(CDCl$_3$): 1.22 (m,1H), 1.82 (m,1H), 2.29 (m,1H), 3.40 (m,1H), 7.47 (s,1H), 7.78 (s,2H). MS (thermospray): M/Z [M+NH$_4$] 441.0; C$_{14}$H$_7$BrCl$_2$F$_3$N$_3$+NH$_4$ requires 440.95.

Purification of the crystallisation mother liquor by reverse phase HPLC on C18 silica, using acetonitrile:water:methanol (50:40:10) as eluant, furnished isomer B as a greyish-white solid, m.p. 126° C. δ(CDCl$_3$): 1.59 (m,1H), 1.62 (m,1H), 2.40 (m,1H), 3.14 (m,1H), 7.39 (s,1H), 7.78 (s,2H). MS (thermospray): M/Z [M+NH$_4$] 441.4; C$_{14}$H$_7$BrCl$_2$F$_3$N$_3$+NH$_4$ requires 440.95.

EXAMPLE 27

3-Cyano-1-(2,6-dichloro-4-trifluoromethylphenyl)-4-(1-trifluoromethylcycfopropyl)pyrazole A solution of the title compound of Preparation 31 (27 g) in xylene (250 ml) was heated under gentle reflux for 16 hours, then the solvent removed by evaporation under reduced pressure. The resulting residue was purified by column chromatography on silica gel (1 Kg), using hexane and then hexane: ether (8:1) as eluants, followed by crystallisation from cyclohexane, to furnish the title compound as a white solid, m.p. 141° C. δ(CDCl$_3$): 1.24 (m,2H), 1.52 (m,2H), 7.72 (s,1H), 7.78 (s,2H). MS (thermospray): M/Z [M+NH$_4$] 431.3; C$_{15}$H$_7$Cl$_2$F$_6$N$_3$+NH$_4$ requires 431.0.

EXAMPLE 28

5-Chloro-3-cyano-4-(2,2-dibromocyclopropyl)-1-(2,6-dichloro-4-trifluoromethylphenyl)pyrazole To a stirred solution of the title compound of Preparation 33 (0.288 g) in dichloromethane (1 ml) was added bromoform (0.275 ml) followed by a solution of sodium hydroxide (0.126 g) in water (0.25 ml) and ethanol (0.05 ml). Benzyltriethylammonium chloride (0.006 g) was then added and the reaction mixture vigorously stirred at room temperature for 48 hours, heated at 50° C. for 7 hours and then stirred at room temperature for 24 hours. After further heating at 50° C. for 24 hours, bromoform (0.275 ml), a solution of sodium hydroxide (0.126 g) in water (0.25 ml) and ethanol (0.05 ml) were added and heating continued for 72 hours. The reaction mixture was cooled, partitioned between ether and water and the aqueous phase separated and extracted with ether (×2) The combined extracts were washed with brine, dried (Na$_2$SO$_4$) and evaporated under reduced pressure, then the residue purified by column chromatography on silica gel, using hexane:dichloromethane (3:2) as eluant, followed by crystallisation from hexane, to afford the title compound as a white solid, m.p. 103.5–104.2° C. δ(CDCl$_3$): 2.31 (dd, 1H), 2.42 (t,1H), 2.78 (dd,1H), 7.80 (s,2H). MS (thermospray): M/Z [M+NH$_4$] 552.9; C$_{14}$H$_5$Br$_2$Cl$_3$F$_3$N$_3$+NH$_4$ requires 552.82.

EXAMPLE 29

4-(2,2-Dibromocyclopropyl)-1-(2,6-dichloro-4-trifluoromethylphenyl-3-trifluoromethylpyrazole To a stirred solution of the title compound of Preparation 36 (0.530 g) in dichloromethane (3 ml) was added bromoform (0.49 ml) followed by a solution of sodium hydroxide (0.226 g) in water (1 ml) and ethanol (0.1 ml).

Benzyltriethylammonium chloride (0.1 g) was then added and the reaction mixture heated at 50° C. for 3 days. Bromoform (0.49 ml), a solution of sodium hydroxide (0.226 g) in water (1 ml) and ethanol (0.1 ml) were added and heating continued for 5 days. The reaction mixture was allowed to cool, partitioned between ether and water and the aqueous phase separated and extracted with ether (×2). The combined organic extracts were washed with brine, dried (Na$_2$SO$_4$) and evaporated under reduced pressure, then the residue purified by column chromatography on silica gel, using hexane:ether:dichloromethane (1:1:2) as eluant, followed by reverse phase HPLC on C18 silica, using acetonitrile:water: methanol (60:30:10) as eluant, to give the title compound as a greenish-yellow gum. δ(CDCl$_3$): 1.87 (t,1H), 2.28 (dd,1H), 2.84 (dd,$_1$ H), 7.40 (s,1H), 7.82 (s,2H). MS (thermospray): M/Z [M+H] 544.6; C$_{14}$H$_6$Br$_2$Cl$_2$F$_6$N$_2$+H requires 544.83.

EXAMPLE 30

4-(2,2-Dibromocyclopropyl)-1-(2,6-dichloro-4-trifluoromethylphenyl)-3-phenylpyrazole To a stirred solution of the title compound of Preparation 40 (0.3 g) in dichloromethane (4 ml) was added bromoform (1 ml), followed by a solution of sodium hydroxide (0.125 g) in water (0.1 ml) and ethanol (0.1 ml). Benzyltriethylammonium chloride (0.022 g) was then added and the reaction mixture heated at 50° C. for 5 days, allowed to cool and partitioned between dichloromethane (10 ml) and water (10 ml). The organic phase was separated, washed with water, dried ($MgSO_4$) and evaporated under reduced pressure, then the residue purified by column chromatography on silica gel (70 g), using an elution gradient of hexane:ether (100:0 to 95:5 to 90:10 to 0:100), followed by reverse phase HPLC on C18 silica, using acetonitrile:water methanol (60:30:10) as eluant. The required fractions from the HPLC column were concentrated and extracted with dichloromethane (3×20 ml). Freeze drying of the combined extracts yielded the title compound as an off-white solid, m.p. 47–48° C. $\delta(CDCl_3)$: 1.86 (t,1H), 2.22 (dd,1H), 2.80 (dd,1H), 7.35 (s,1H), 7.40–7.60 (m,3H), 7.75 (s,2H), 7.92 (d,2H). MS (thermospray): M/Z [M+H] 553.5; $C_{19}H_{11}Br_2Cl_2F_3N_2+H$ requires 552.87.

EXAMPLE 31

4-(1-Chlorodifluoromethylcyclopropyl)-3-cyano-1-(2,6-dichloro-4-trifluoromethylphenyl)pyrazole Obtained from the title compound of Preparation 44, by analogy with Example 27 but heating for 4 hours, using hexane:ether (8:1) as chromatographic eluant and with no subsequent crystallisation, as a white solid, m.p. 124–125° C. $\delta(CDCl_3)$: 1.24 (m,2H), 1.58 (m,2H), 7.74 ($s,_1H$), 7.74 (s, 2H). MS (thermospray): M/Z [M+$NH_4$] 446.9; $C_{15}H_7Cl_3F_5N_3+NH_4$ requires 447.0.

EXAMPLE 32

3-Cyano-1-(2,6-dichloro-4-trifluoromethylphenyl)-4-(1-ethylcyclopropyl)pyrazole

A 0.467 M solution of diazomethane in ether (30 ml) was added over 2 minutes to a stirred solution of the title compound of Preparation 47 (3 g) and palladium(II) acetate (0.025 g) in ether (5 ml) and the resulting mixture stirred at room temperature for 18 hours. The reaction mixture was filtered, treated with additional quantities of the ethereal diazomethane solution (30 ml) and palladium(I) acetate (0.025 g), stirred for 4 hours more, filtered then further treated with the ethereal diazomethane solution (30 ml) and palladium(II) acetate (0.025 g), stirred for 40 hours more, filtered then further treated with the ethereal diazomethane solution (30 ml) and palladium(II) acetate (0.025 g), stirred for 88 hours more, filtered then further treated with the ethereal diazomethane solution (30 ml) and palladium(II) acetate (0.025 g), stirred for 2 hours more, filtered then further treated with the ethereal diazomethane solution (30 ml) and palladium(II) acetate (0.025 g), stirred for 18 hours more and then evaporated under reduced pressure. The residue was purified by reverse phase HPLC on C18 silica, using acetonitrile:water (60:40) as eluant, to provide the title compound as a white solid, m.p. 118–119° C. $\delta(CDCl_3)$: 0.80 (m,2H), 0.90 (m,5H), 1.63 (m,2H), 7.44 (s,1H), 7.77 (s,2H). MS (thermospray): M/Z [M+$NH_4$] 390.8; $C_{16}H_{12}Cl_2F_3N_3+NH_4$ requires 391.1.

EXAMPLE 33

3-Cyano-4-(2,2-dibromo-1-ethylcyclopropyl)-1-(2,6-dichloro-4-trifluoromethylphenyl)pyrazole A solution of the title compound of Preparation 47 (105 mg) and phenyltribromomethylmercury (160 mg) in toluene (4 ml) was heated at 70° C. for 2 hours, then a solution of phenyltribromomethylmercury (1 80 mg) in toluene (2 ml) was added and the mixture heated at 70° C. for 16 hours, more phenyltribromomethylmercury (230 mg) was added and the mixture heated at 70° C. for 4 hours, yet more phenyltribromomethylmercury (310 mg) was added and the mixture heated at 70° C. for 2 hours, still more phenyltribromomethylmercury (310 mg) was added and the mixture heated at 70° C. for 16 hours, then allowed to cool. The resulting mixture was filtered through silica gel (10 g), using hexane and then dichloromethane as eluants, and the required eluate fractions evaporated under reduced pressure. The residue was purified by column chromatography on silica gel (10 g), using dichloromethane:hexane (1:4) as eluant, followed by reverse phase HPLC on C18 silica, using acetonitrile:water:methanol (60:30:10) as eluant, to furnish the title compound as a white solid, m.p. 107–108° C. $\delta(CDCl_3)$: 1.04 (t,3H), 1.90 (m,2H), 2.19 (m,2H), 7.62 (s,2H), 7.79 (s,2H). MS (thermospray): M/Z [M+H] 530.0; $C_{16}H_{10}Br_2Cl_2F_3N_3+H$ requires 529.9.

EXAMPLE 34

3-Cyano-1-(2,6-dichloro-4-trifluoromethylphenyl)-4-(1-pentafluoroethylcyclopropyl)pyrazole Obtained from the title compound of Preparation 50, by analogy with Example 31 but using reverse phase HPLC on C18 silica with acetonitrile:water:methanol (60:30:10) as eluant, as a white solid, m.p. 105–106° C. $\delta(CDCl_3)$: 1.24 (m,2H), 1.55 (m,2H), 7.67 (s,1H), 7.77 (s,2H). MS (electrospray): M/Z (M+H] 464.0; $C_{16}H_7Cl_2F_8N_3+H$ requires 464.0.

EXAMPLE 35

3-Cyano-1-(2,6-dichloro-4-trifluoromethylphenyl)-4-(1-heptafluoropropylcyclopropyl)pyrazole Obtained from the title compound of Preparation 53, by analogy with Example 31 but heating for 3 hours and effecting post-chromatographic crystallisation from cyclohexane, as a white solid, m.p. 95–96° C. $\delta(CDCl_3)$: 1.23 (m,2H), 1.54 (m,2H), 7.65 (s,1H), 7.74 (s,2H). MS (thermospray): M/Z [M+H] 514.2; $C_{17}H_7Cl_2F_{10}N_3+H$ requires 514.0.

EXAMPLE 36

5-Amino-3-cyano-1-(2,6-dichloro-4-trifluoromethylphenyl)(1-trifluoromethylcyclopronyl)pyrazole A solution of the title compound of Preparation 55 (130 mg) in a mixture of xylene (8 ml) and toluene (1 ml) was heated under gentle reflux for 7 hours, then allowed to stand at room temperature for 16 hours. The solvent was removed by evaporation under reduced pressure and the resulting residue purified by reverse phase HPLC on C18 silica, using acetonitrile:water:methanol (45:45:10) as eluant, to afford the title compound as a white solid, m.p. 178–179° C. $\delta(CDCl_3)$: 1.13 (m,2H), 1.48 (m,2H), 3.91 (br.s,2H), 7.80 (s,2H). MS (thermospray): M/Z [M+H] 429.1; $C_{15}H_8Cl_2F_6N_4+H$ requires 429.0.

EXAMPLE 37

1-[(3-Chloro-5-trifluoromethyl)pyridin-2-yl]-3-cyano-4-(2,2-dibromocyclopropyl)pyrazole A solution of the title compound of Preparation 58 (0.50 g) and phenyltribromomethylmercury (1.0 g) in toluene (5 ml) was heated at 70° C. under nitrogen for 1.5 hours. More phenyltribromomethylmercury (0.50 g) was added and heating continued for a further 72 hours. The resulting mixture was allowed to cool, partitioned between ether and water, and the aqueous phase separated and extracted with ether (×2). The combined extracts were washed successively with water and saturated brine, dried (MgSO$_4$) and evaporated under reduced pressure. The crude product (0.50 g), a brown oil, was purified by column chromatography on silica gel, using hexane:ethyl acetate (9:1) as eluant, to give the title compound as a yellow solid, m.p. 81–83° C. δ(CDCl$_3$): 2.05 (t,1H), 2.33 (dd,1H), 2.85 (dd,1H), 8.20 (s,1H), 8.23 (s,1H), 8.70 (s,1H), MS (thermospray): M/Z [M+H] 467.9; $C_{13}H_6Br_2ClF_3N_4$+H requires 467.9.

EXAMPLE 38

3-Acetyl-4-(2,2-dibromocyclopropyl)-1-(2,6-dichloro-4-trifluoromethylphenyl)pyrazole A solution of the title compound of Example 2 (3.42 g) in ether (25 ml) was added to a stirred, ice-cooled mixture of a 3.0M solution of methylmagnesium iodide in ether (2.26 ml) and anhydrous ether (25 ml) under nitrogen, whilst maintaining the reaction temperature below 2° C. The reaction mixture was allowed to warm to room temperature, heated under reflux for 2 hours and then treated with more (0.5 ml) of the 3 M ethereal methylmagnesium iodide solution. This mixture was heated under reflux for 1 hour and then stirred at room temperature for 18 hours. A further quantity (1 ml) of the ethereal methylmagnesium iodide solution was added and the resulting mixture heated under reflux for 3 hours, then poured into a stirred mixture of concentrated hydrochloric acid (2 ml) and ice (10 g). Extraction with ether (×3), followed by washing of the combined extracts with brine, drying (MgSO$_4$) and evaporation under reduced pressure, gave the crude product which was purified by column chromatography on silica gel, using hexane:dichloromethane (1:1) as eluant. followed by crystallisation from hexane, to provide the title compound as a pale yellow solid, m.p. 149.5–150.3° C. δ(CDCl$_3$): 1.78 (dd,1H), 2.24 (dd,1H), 2.69 (s,3H), 3.37 (dd,1H), 7.34 (s,1H), 7.78 (s,2H). MS (thermospray): M/Z [M+NH$_4$] 536.3; $C_{15}H_9Br_2Cl_2F_3N_2O$+NH$_4$ requires 535.88.

EXAMPLE 39

4-(2,2-Dibromocyclopropyl)-1-(2,6-dichloro-4-trifluoromethylphenyl)-3-(1-hydroxyethyl)pyrazole A 1M solution of borane:tetrahydrofuran complex in tetrahydrofuran (4.61 ml) was added to a stirred solution of the title compound of Example 38 (0.40 g) in anhydrous tetrahydrofuran (5 ml) at about −50° C. under nitrogen. The reaction mixture was allowed to warm to room temperature, stirred for a further 4 hours and then evaporated under reduced pressure. The residue was purified by column chromatography on silica gel, using hexane:ether (3:1) as eluant, to yield the title compound as an oily white solid. δ(CDCl$_3$): 1.55 (s,1H), 1.75 (d,3H), 1.80 (t,1H), 2.20 (dd, 1H), 2.95 (dd,1H), 5.20 (m,1H), 7.25 (s,1 H), 7.70 (s,2H). MS (thermospray): M/Z [M+H] 521.0; $C_{15}H_{11}Br_2Cl_2F_3N_2O$+H requires 520.86.

EXAMPLE 40

4-(2,2-Dibromocyclopropyl)-1-(2,6-dichloro-4-trifluoromethylphenyl)-3-ethylpyrazole Triethylsilane (0.22 ml) was added to a stirred solution of the title compound of Example 39 (0.18 g) in dichloromethane (5 ml), at about −75° C., whilst maintaining the reaction temperature below −70° C. Boron trifluoride diethyl etherate (0.17 ml) was added and the reaction mixture allowed to warm to room temperature, then stirred for a further 24 hours. Next, the mixture was cooled to about −70° C., more triethylsilane (0.22 ml) and boron trifluoride diethyl etherate (0. 17 ml) added, the cooling bath removed and stirring continued at room temperature for 4 days. The resulting mixture was washed with dilute hydrochloric acid and the aqueous phase extracted with dichloromethane (×2). The combined organic solutions were washed with brine, dried (Na$_2$SO$_4$) and evaporated under reduced pressure, then the residue purified by column chromatography on silica gel, using hexane:ether (2:1) as eluant, to furnish the title compound as a colourless oil. δ(CDCl$_3$): 1.45 (t,3H), 1.80 (t,1H), 2.20 (dd,1H), 2.65 (dd,$_1$H), 2.85 (q,2H), 7.20 (s,1H), 7.70 (s,2H). MS (thermospray): M/Z [M+H] 504.9; $C_{15}H_{11}Br_2Cl_2F_3N_2$+H requires 504.87.

EXAMPLE 41

4-(2,2-Dibromocyclopropyl)-1-(2,6-dichloro-4-trifluoromethylphenyl)-3-(2-hydroxyprop-2-yl)pyrazol A solution of the title compound of Example 38 (0.30 g) in ether (5 ml) was added to a stirred, ice-cooled mixture of a 3.0M solution of methylmagnesium iodide (0.21 ml) and anhydrous ether (5 ml) under nitrogen, whilst maintaining the reaction temperature below 2° C. The reaction mixture was allowed to warm to room temperature, heated under reflux for 1 hour, allowed to cool, then poured into a stirred mixture of concentrated hydrochloric acid (2 ml) and ice (10 g). Extraction with ether (×3), followed by washing of the combined extracts with brine, drying (MgSO$_4$) and evaporation under reduced pressure, afforded the crude product which was crystallised from toluene to give the title compound as a white solid, m.p. 132.1–132.7° C. δ(CDCl$_3$): 1.80 (s,6H), 1.82 (t,1H), 2.20 (dd,1H), 2.55 (s,1 H), 3.05 (dd,1H), 7.20 (s,1H), 7.70 (s,2H). MS (thermospray): M/Z [M+H] 534.4; $C_{16}H_{13}Br_2Cl_2F_3N_2O$+H requires 534.88.

EXAMPLE 42

4-(2,2-Dibromocyclopropyl)-1-(2,6-dichloro-4-trifluoromethylphenyl)-3-(prop-2-yl)pyrazole Triethylsilane (0.14 ml) was added to a stirred solution of the title compound of Example 41 (0.115 g) in dichloromethane (5 ml) at about −75° C., whilst maintaining the reaction temperature below −70° C. Boron trifluoride diethyl etherate (0.11 ml) was added and the reaction mixture kept at about −70° C. for 2.5 hours, before being allowed to warm to room temperature. After a further 24 hours, the mixture was washed with dilute hydrochloric acid and the aqueous phase then extracted with ether (×2). The combined organic solutions were washed with brine, dried (Na$_2$SO$_4$) and evaporated under reduced pressure to produce the crude product which was purified by column chromatography on silica gel, using hexane:ether (4:1) as eluant, to yield the title compound as a colourless oil. δ(CDCl$_3$): 1.40 (d,6H), 1.80 (t,1H), 2.20 (dd,1H), 2.70 (dd,1H), 3.20 (sept., 1H), 7.15 (s,1H), 7.70 (s,2H). MS (thermospray): M/Z [M+] 518.4; $C_{16}H_{13}Br_2Cl_2F_3N_2$+H requires 518.89.

EXAMPLE 43

4-(2,2-Dibromocyclopropyl)-1-(2,6-dichloro-4-trifluoromethylphenyl)-3-formylpyrazole A 1M solution of diisobutylaluminium hydride in hexane (1.5 ml) was added dropwise over 5 minutes to a stirred, ice-cooled solution of the title compound of Example 2 (0.50 g) in anhydrous tetrahydrofuran (15 ml). After 1 hour, the reaction mixture was treated with a further quantity (2.25 ml) of the hydride solution, stirred for 18 hours and then poured into acidified aqueous methanol. This mixture was extracted with ether (×2), then the combined extracts washed successively with water and brine, dried (MgSO$_4$) and evaporated under reduced pressure. The resulting residue was purified by column chromatography on silica gel, using hexane:ethyl acetate (9:1) as eluant, to afford the title compound as an oil. δ(CDCl$_3$): 1.80 (dd,1 H), 2.28 (dd,1H), 3.32 (dd,1H), 7.39 (s,1H), 7.78 (s,2H), 10.19 (s,1H). MS (thermospray): M/Z [M+H] 504.7; $C_{14}H_7Br_2Cl_2F_3N_2O$+H requires 504.83.

EXAMPLE 44

4-(2.2-Dibromocyclopropyl)-1-(2,6-dichloro-4-trifluorormethylphenyl)-3-difluoromethylpyrazole Diethylaminosulphur trifluoride (0.13 g) was added to a stirred solution of the title compound of Example 43 (0.20 g) in dichloromethane (5 ml). After a further 3 hours at room temperature, the reaction mixture was diluted with dichloromethane, washed with water (×2), dried (MgSO$_4$) and evaporated under reduced pressure. The residue was purified by column chromatography on silica gel, using hexane:ethyl acetate (19:1) as eluant, to provide the title compound as a white solid, m.p. 99–101° C. δ(CDCl$_3$): 1.85 (t,1H), 2.25 (dd,1H), 2.95 (dd,$_1$H), 6.87 (t,1H), 7.38 (s,1H), 7.74 (s,2H). MS (thermospray): M/Z [M+H] 526.5; $C_{14}H_7Br_2Cl_2F_5N_2$+H requires 526.84.

EXAMPLE 45

4-(2,2-Dibromocyclopropyl)-3-dichloromethyl-1-(2, 6-dichloro-4-trifluoromethylphenyl)pyrazole Phosphorus pentachloride (0.17 g) was added to a stirred solution of the title compound of Example 43 (0.20 g) in ether (10 ml). After a further 24 hours, more phosphorous pentachloride (0.17 g) was added and the reaction mixture stirred for a further 24 hours, before being evaporated under reduced pressure. Purification of the residue by column chromatography on silica gel, using hexane:ethyl acetate (19:1) as eluant, furnished the title compound as a white solid, m.p. 87–89° C. δ(CDCl$_3$): 1.90 (t,1H), 2.29 (dd,1H), 3.12 (dd,1H), 6.96 (s,1H), 7.30 (s,1H), 7.72 (s,2H). MS (APCI): M/Z [M+H] 559.2; $C_{14}H_7Br_2Cl_4F_3N_2$+H requires 558.78.

EXAMPLE 46

3-Cyano-4-(2,2-dibromocyclopropyl)-1-(2,4,6-trichlorophenyl)pyrazole

A mixture of the title compound of Preparation 61 (2.0 g), 96% bromoform stabilised with 1 to 3% ethanol (6.5 ml), sodium hydroxide (1.0 g), water (1.0 ml), ethanol (0.14 ml), dichloromethane (6.5 ml) and benzyltriethylammonium chloride (80 mg) was rapidly stirred under gentle reflux at about 40° C. for 6 hours, then at room temperature for 18 hours and again at about 40° C. for 6 hours. More sodium hydroxide (0.3 g), water (0.6 ml) and quaternary ammonium salt catalyst (130 mg) were added and the reaction mixture vigorously stirred at about 40° C. for 6 hours and then at room temperature for 18 hours. More catalyst (100 mg) was added and the reaction mixture stirred at about 40° C. for 6 hours and then at room temperature for 66 hours. Still more catalyst (100 mg) and more dichloromethane (2.0 ml) were added and the reaction mixture stirred at about 40° C. for 6 hours, at room temperature for 18 hours, at about 40° C. for 7 hours, at room temperature for 18 hours, at about 40° C. for 7 hours and at room temperature for 18 hours. Finally, more 96% bromoform (3.0 ml), 50% aqueous sodium hydroxide solution (0.5 ml), dichloromethane (3.0 ml) and catalyst (150 mg) were added and the resulting mixture stirred at room temperature for 1 week, then partitioned between dichloromethane (100 ml) and water (50 ml). The separated organic phase was washed with water (50 ml), dried (Na$_2$SO$_4$) and evaporated under reduced pressure to produce a black gum which was purified by column chromatography on silica gel (100 g), using hexane and then hexane:ether:dichloromethane (8:1:1) as eluants, to afford the title compound as a very pale yellow solid, m.p. 164° C. δ(CDCl$_3$): 2.02 (t,1H), 2.34 (dd,$_1$H), 2.87 (dd,1H), 7.48 (s,1H), 7.51 (s,2H). MS (thermospray): M/Z [M+NH$_4$] 484.6; $C_{13}H_6Br_2Cl_3N_3$ +NH$_4$ requires 484.8.

EXAMPLE 47

3-Cyano-4-(2,2-dichlorocyclopropyl)-1-(2,4,6-trichlorophenyl)pyrazole

A mixture of the title compound of Preparation 61 (2.0 g), chloroform (6.0 ml), sodium hydroxide (1.0 g), water (1.0 ml), ethanol (0.2 ml), dichloromethane (6.5 ml) and benzyltriethylammonium chloride (150 mg) was rapidly stirred at about 40° C. for 66 hours. More sodium hydroxide (0.5 g), water 1.0 ml), dichloromethane (4 ml) and quaternary ammonium salt catalyst (180 mg) were added and the reaction mixture stirred at about 40° C. for 90 hours. Yet more catalyst (150mg), dichloromethane (5.0 ml), 50% aqueous sodium hydroxide solution (0.5 m) and chloroform (3.0 ml) were added and the resulting mixture stirred at about 36° C. for 10 days, then partitioned between dichloromethane (100 ml) and water (50 ml). The separated organic phase was washed with water (50 ml), dried (Na$_2$SO$_4$) and evaporated under reduced pressure to yield a black gum which was purified by column chromatography on silica gel (80 g), using hexane:ether:dichloromethane (8:1:1) as eluant, to give the title compound as a pale yellow solid, m.p. 157.8° C. δ(CDCl$_3$): 1.85 (t,1H), 2.19 (dd,1H), 2.85 (dd,1H), 7.49 (s,1H), 7.52 (s,2H). MS (thermospray): [M/Z+NH$_4$] 396.8; $C_{13}H_6Cl_5N_3$ +NH$_4$ requires 396.9.

EXAMPLE 48

5-Amino-3-cyano-4- (2,2-dichlorocyclopropyl)-1-(2, 6-dichloro-4-pentafluorothiophenyl)pyrazole A vigorously stirred mixture of 5-amino-3-cyano-1-(2,6-dichloro4-pentafluorothiophenyl)-4-ethenylprazole (WO-A-97/07102; 0.50 g), chloroform (3.0 ml), a solution of sodium hydroxide (0.25 g) in water (0.25 ml), ethanol (2 drops), dichloromethane (2.0 ml) and benzyltriethylammonium chloride (25 mg) was heated under reflux for 18 hours, then more chloroform (3.0 ml) and quaternary ammonium salt catalyst (25 mg) added and stirring under reflux continued for 78 hours. Still more chloroform (3.0 ml) and catalyst (25 mg) were added and the resulting mixture stirred under reflux for 4 days, then partitioned between dichloromethane (30 ml) and water (30 ml). The separated organic phase was washed with water (2×20 ml) and saturated brine (20 ml), dried (Na$_2$SO$_4$) and evaporated under reduced pressure to give a dark brown oil. This crude material was purified as follows: (i) pre-absorption onto silica gel (1.5 g) using dichloromethane as solvent, followed by column chromatography on silica gel (20 g) using hexane:ethyl acetate (7:3) as eluant; (ii) reverse phase HPLC on C18 silica, using acetonitrile:water (70:30) as eluant; and (iii) further reverse phase HPLC on C18 silica, using acetonitrile:methanol:water (50:10:40) as eluant; to provide the title compound as an off-white solid, m.p. 90–95°C. δ(CDCl$_3$): 2.23 (m,2H), 2.56 (t,1H), 3.84 (br.s,2H), 7.83 (s,2H). MS (thermospray): M/Z [M+H] 487.3; $C_{13}H_7Cl_4F_5N_4S$ +H requires 486.9.

EXAMPLE 49

3-Cyano-4-(2,2-dichlorocyclopropyl)-1-(2,6-dichloro-4-pentafluorothiophenyl)pyrazole The reaction was conducted using the procedure of Example 48 and 3-cyano-1-(2,6-dichloro-4-pentafluorothiophenyl)-4-ethenylpyrazole (WO-A-97/07102) as starting material. The crude dark brown oil was purified as follows: (i) pre-absorption onto silica gel (1.5 g) using dichloromethane as solvent, followed by column chromatography on silica gel (15 g) using hexane:ether:dichloromethane (8:1:1) as eluant; (ii) trituration of the resulting pale yellow oil with diisopropyl ether, followed by filtration and evaporation under reduced pressure of the filtrate to give a yellow oil which solidified on standing; (iii) reverse phase HPLC on C18 silica, using acetonitrile:water (70:30) as eluant; (iv) further reverse phase HPLC on C18 silica pre-washed with hexane, using hexane and then dichloromethane as eluants; and (v) dissolution of the resulting oil in methanol, then addition of water to the solution until turbid followed by chilling, to furnish the title compound as a white solid, m.p. 78–80° C. δ(CDCl$_3$): 1.87 (t,1H), 2.20 (m,1H), 2.85 (m,1H), 7.53 (s,1H) 7.93 (s,2H). MS (thermospray): M/Z [M+NH$_4$] 489.1; $C_{13}H_6Cl_4F5N_3S$ +NH$_4$ requires 488.9.

Preparation 1

5-Amino-3-cyano-1-(2,6-dichloro-4-trifluoromethylphenyl)-4-iodopyrazole

N-Iodosuccinimide (3.52 g) was added in portions, over 5 minutes, to a stirred solution of 5-amino-3-cyano-1-(2,6-dichloro-4-trifluoromethylphenyl)pyrazole (EP-A-0295117; 5.0 g) in acetonitrile (60 ml) at room temperature. After being stirred for 1 hour, the reaction mixture was evaporated under reduced pressure to provide the required crude product (8.2 g) which, despite containing succinimide, may be used without further purification.

If desired, purification may be effected by partitioning the crude product between dichloromethane and water, separating and drying (MgSO$_4$) the organic phase and evaporating it under reduced pressure, then triturating the resulting yellow solid with hexane to give the title compound as a white solid, m.p. 213° C. (decomp.).

Preparation 2

5-Amino-3-cyano-1-(2,6-dichloro-4-trifluoromethylphenyl)-4,-ethenylpyrazole

Tri-n-butyl(vinyl)tin (4.25 g) and tetrakis(triphenylphosphine)palladium(0) (0.3 g) were added to a stirred solution of the title compound of Preparation 1 (2.09 g) in dimethylformamide (10 ml) at room temperature and the resulting mixture heated at 75° C. for 1 hour, then stirred at room temperature for a further 60 hours, before being diluted with water. The mixture was extracted with ether and the combined extracts washed with brine, dried (MgSO$_4$) and evaporated under reduced pressure to furnish the crude product (6.0 g) as a black oil, which was purified by column chromatography on silica gel (200 g), using hexane: dichloromethane (1:1) as eluant, to afford the title compound as a buff solid, m.p. 186–187° C. δ(CDCl$_3$): 3.85 (s,2H), 5.41 (d,1H), 5.70 (d,1H), 6.52 (dd,1H), 7.80 (s,2H). MS (thermospray): M/Z [M+H] 347.0; $C_{13}H_7Cl_2F_3N_4$+H requires 347.0.

Preparation 3

3-Cyano-1-(2,6-dichloro-4-trifluoromethylphenyl)-4-iodopyrazole t-Butyl nitrite (144 ml) was added over 30 minutes to a stirred solution of the title compound of Preparation 1 (90 g) in tetrahydrofuran (720 ml) at 65° C. After 3 hours at 65° C., the reaction mixture was allowed to cool and evaporated under reduced pressure, then the residue crystallised from propanol to give the title compound as a white solid, m.p. 83–84° C. δ(CDCl$_3$): 7.70 (s,1H), 7.79 (s,2H). MS (thermospray): M/Z [M+NH$_4$] 448.8; $C_{11}H_3Cl_2F_3IN_3$+NH$_4$ requires 4.48.9.

Preparation 4

3-Cyano-1-(2,6-dichloro-4-trifluoromethylphenyl)-4-ethenylpyrazole

A solution of the title compound of Preparation 3 (58 g), tri-n-butyl(vinyl)tin (116 ml) and tetrakis(triphenylphosphine)palladium(0) (3.5 g) in dimethylformamide (350 ml) was stirred at 75° C. for 3 hours and then allowed to cool. The reaction mixture was partitioned between ether (600 ml) and water (600 ml), then the organic phase washed successively with water (×5) and brine, dried (Na$_2$SO$_4$) and evaporated under reduced pressure. Crystallisation of the residue from propan-2-ol provided the title compound as a pale brown solid, m.p. 75–76° C. δ(CDCl$_3$): 5.50 (d,1H), 5.94 (d,1H), 6.64 (dd,1H), 7.64 (s,1H), 7.77 (s,2H). MS (thermospray): M/Z [M+NH$_4$] 349.5; $C_{13}H_6Cl_2F_3N_3$+NH$_4$ requires 349.02.

Preparation 5

5-Amino-3-cyano-1-(2,6-dichloro-4-pentafluorothiophenyl)-4-iodopyrazole

N-Iodosuccinimide (11.5 g) was added in four portions, over 5 minutes, to a stirred solution of 5-amino-3-cyano-1-(2,6-dichloro-4-pentafluorothiophenyl)pyrazole (WO-A-93/06089; 18.95 g) in acetonitrile (100 ml) at room temperature. After a further 15 minutes, the reaction mixture was evaporated under reduced pressure and the residual solid treated with a mixture of dichloromethane and water. The insoluble material was collected by filtration and dissolved in ethyl acetate, then this solution was dried (Na$_2$SO$_4$) and evaporated under reduced pressure to furnish the title compound as a buff solid, m.p. 253° C. δ(CDCl$_3$): 3.94 (br.s,2H), 7.92 (s,2H). MS (thermospray): M/Z [M+NH$_4$] 521.9; $C_{10}H_4Cl_2F_5IN_4S$+NH$_4$ requires 521.88.

Preparation 6

5-Amino-3-cyano-1-(2,6-dichloro-4-pentafluorothiophenyl)-4-ethenylpyrazole

Tri-n-butyl(vinyl)tin (4.5 ml) was added to a stirred, degassed solution of the title compound of Preparation 5 (5.05 g) and tetrakis(triphenylphosphine) palladium(0) (0.175 g) in dimethylformamide (32 ml) at room temperature and the resulting mixture heated to 70° C. over 30 minutes. After a further 1 hour at 70 ° C. tri-n-butyl(vinyl)tin (4.5 ml) and tetrakis(triphenylphosphine)palladium(0) (0.175 g) were added and the reaction mixture was heated at 70° C. for 1 hour, then evaporated under reduced pressure. The residue was partitioned between ether and water, then the separated organic phase combined with ether extracts of the aqueous phase, washed with brine, dried (MgSO$_4$) and evaporated under reduced pressure to give a brown paste which was triturated with hexane. The resulting brown solid was treated with ethyl acetate, the mixture filtered, the filtrate evaporated under reduced pressure and the residue crystallised from toluene to yield the title compound as a buff solid, m.p. 227–228° C. δ(CDCl$_3$): 3.86 (s,2H), 5.41 (d,1H), 5.68 (d,1H), 6.50 (dd,1H), 7.92 (s,2H). MS (thermospray): M/Z [M+H] 405.1; C$_{12}$H$_7$Cl$_2$F$_5$N$_4$S+H requires 404.98.

Preparation 7

3-Cyano-1-(2,6-dichloro-4-pentafluorothiophenyl)-4-iodopyrazole

A solution of t-butyl nitrite (3.1 g) in tetrahydrofuran (15 ml) was added dropwise over 30 minutes to a stirred solution of the title compound of Preparation 5 (2.5 g) in tetrahydrofuran (35 ml), then the reaction mixture was evaporated under reduced pressure. Crystallisation of the residue from propan-2-ol afforded the title compound as a pinkish solid, m.p. 179–180° C. δ(CDCl$_3$): 7.66 (s,1H), 7.90 (s,2H). MS (thermospray): M/Z[M+NH$_4$] 506.4; C$_{10}$H$_3$Cl$_2$F$_5$IN$_3$S+NH$_4$ requires 506.87.

Preparation 8

3-Cyano-1-(2,6-dichloro-4-pentafluorothiophenyl)-4-ethenylpyrazole

Tri-n-butyl(vinyl)tin (4.2 ml) was added to a stirred, degassed solution of the title compound of Preparation 7 (1.23 g) and tetrakis(triphenylphosphine) palladium(0) (0.09 g) in dimethylformamide (32 ml) at room temperature and the resulting mixture heated at 70° C. for 1.5 hours, before being evaporated under reduced pressure. The residue was triturated with hexane and the resulting solid purified by dissolution in dichloromethane and column chromatography of the solution on silica gel (60 g), using hexane and then hexane:dichloromethane (80:20) as eluants, to yield the title compound as a white solid, m.p. 156° C. δ(CDCl$_3$): 5.50 (d,1H), 5.95 (d,1H), 6.63 (dd,1H), 7.77 (s,1H), 7.92 (s,2H). MS (thermospray): M/Z [M+NH$_4$] 406.8; C$_{12}$H$_6$Cl$_2$F$_5$N$_3$S+NH$_4$ requires 406.99.

Preparation 9

3-Cyano-1-(2,6-dichloro-4-trifluoromethylphenyl)-4-formylpyrazole

A solution of the title compound of Preparation 4 (0.1 g), a 2.5 wt. % solution of osmium tetroxide in t-butanol (50 µl) and 4-methylmorpholine-N-oxide (0.005 g) in 90% aqueous acetone (50 ml) was stirred at room temperature for 16 hours. Sodium metaperiodate (0.005 g) was added and the reaction mixture stirred for a further 16 hours, then evaporated under reduced pressure. The residue was partitioned between ether and saturated aqueous sodium bicarbonate solution, the aqueous phase separated and extracted with ether, then the combined ether extracts dried (Na$_2$SO$_4$) and evaporated under reduced pressure. The residue was purified by column chromatography on silica gel (5 g), using dichloromethane as eluant, to give the title compound as a beige solid, m.p. 167.5–168.5° C. δ(CDCl$_3$): 7.80 (s,2H), 8.18 (s,1H), 10.08 (s,1H). MS (thermospray): M/Z [M+NH$_4$] 351.3; C$_{12}$H$_4$Cl$_2$F$_3$N$_3$O+NH$_4$ requires 351.0.

Preparation 10

3-Cyano-1-(2,6-dichloro-4-trifluoromethylphenyl)-4-(2-methylpropen-1-yl)pyrazole A 2.5M solution of n-butyllithium in hexane (0.9 ml) was added to a stirred solution of prop-2-yltriphenylphosphonium iodide (0.97 g) in anhydrous ether (10 ml) at room temperature to produce a dark red solution. A solution of the title compound of Preparation 9 (0.6 g) in ether (20 ml) was added and the reaction mixture stirred for 2 hours, washed with water (20 ml), dried (MgSO$_4$) and evaporated under reduced pressure. The residue was purified by column chromatography on silica gel, using dichloromethane as eluant, to provide the title compound as a pale tan solid, m.p. 72–74° C. δ(CDCl$_3$): 1.90 (s,3H), 1.99 (s,3H), 6.17 (s,1H), 7.60 (s,1H), 7.77 (s,2H). MS (thermospray): M/Z [M+NH$_4$] 360.2; C$_{15}$H$_{10}$Cl$_2$F$_3$N$_3$+NH$_4$ requires 360.03.

Preparation 11

5-Amino-3-cyano-1-(2,6-dichloro-4-trifluoromethylphenyl)-4-trimethylsilylethynylpyrazole Trimethylsilylacetylene (3 ml), cuprous iodide (150 mg) and bis(triphenyl-phosphine) palladium(II) chloride (300 mg) were added to a stirred solution of the title compound of Preparation 1 (6.96 g) in a mixture of triethylamine (30 ml) and dimethylformamide (6 ml) at room temperature and the resulting mixture heated at 50–60° C. for 1 hour. More trimethylsilylacetylene (0.3 ml) was added, then the reaction mixture stirred for 30 minutes at 50–60° C. allowed to cool and diluted with water (250 ml). This mixture was extracted with ether (250 ml), using brine to facilitate phase separation, and the aqueous phase separated and extracted with ether (250 ml). The combined ether extracts were dried (MgSO$_4$) and evaporated under reduced pressure to furnish a gum (4.67 g) which was purified by column chromatography on silica gel, using hexane:dichloromethane (1:1) as eluant, followed by crystallisation of the required material from hexane-ether, thus affording the title compound as a white solid, m.p. 181–182° C. δ(CDCl$_3$): 0.20 (s,9H), 4.10 (br.s,2H), 7.70 (s,2H). MS (thermospray): M/Z [M+NH$_4$] 434.2; C$_{16}$H$_{13}$Cl$_2$F$_3$N$_4$Si+NH$_4$ requires 434.0.

Preparation 12

5-Amino-3-cyano-1-(2,6-dichloro-4-trifluoromethylphenyl)-4-ethynylpyrazole

Potassium carbonate (1.0 g) was added to a stirred solution of the title compound of Preparation 11 (2.0 g ) in methanol (30 ml). After 10 minutes at room temperature, the reaction mixture was partitioned between ether (100 ml) and water (100 ml), then the organic phase separated, washed with brine (100 ml), dried (MgSO$_4$) and evaporated under reduced pressure. The residue was purified by column chromatography on silica gel, using dichicromethane as eluant, followed by crystallisation from ether, to give the title compound as a white solid, m.p. 215–216° C. δ(CDCl$_3$): 3.49 (s,1H), 4.20 (br.s,2H), 7.80 (s,2H). MS (thermospray): M/Z [M+NH$_4$] 362.4; C$_{13}$H$_5$Cl$_2$F$_3$N$_4$+NH$_4$ requires 362.0.

Preparation 13

4-Acetyl-5-amino-3-cyano-1-(2,6-dichloro-4-trifuoromethylphenyl)-pyrazole p-Toluenesulphonic acid (0.5 g) was added to a stirred solution of the title compound of Preparation 12 (0.345 g) in acetonitrile (5 ml). After a further 2 hours at room temperature, the reaction mixture was partitioned between ether (100 ml) and water (100 ml), then the organic phase separated, washed successively with saturated aqueous sodium bicarbonate solution and brine, dried (Na$_2$SO$_4$) and evaporated under reduced pressure. The residue was purified by column chromatography on silica gel (40 g), using hexane:dichloromethane (1:10) as eluant, to provide the title compound as a white crystalline solid, m.p. 200–201° C. δ(CDCl$_3$): 2.65 (s,3H), 5.83 (br.s,2H), 7.82 (s,2H). MS (thermospray): M/Z [M+NH$_4$] 380.4; C$_{13}$H$_7$Cl$_2$F$_3$N$_4$O+NH$_4$ requires 380.03.

Preparation 14

4-Acetyl-3-cyano-1-(2,6-dichloro-4trifluoromethylphenyl)pyrazole t-Butyl nitrite (0.0262 ml) was added dropwise to a stirred solution of the title compound of Preparation 13 (0.4 g) in tetrahydrofuran (2 ml). The reaction mixture was heated under reflux for 30 minutes and then applied to a silica gel (1.0 g) column. Elution with tetrahydrofuran yielded the title compound as a white solid, m.p. 166–168° C. δ(CDCl$_3$): 2.67 (s,3H), 7.80 (s,2H), 8.12 (s,1H). MS (thermospray): M/Z [M+NH$_4$] 365.0; C$_{13}$H$_6$Cl$_2$F$_3$N$_3$O+NH$_4$ requires 365.02

Preparation 15

3-Cyano-1-(2,6-dichloro-4-trifluoromethylphenyl-4-(1-methylethenyl)-pyrazole A 2.5M solution of n-butyllithium in tetrahydrofuran (0.64 ml) was added to a stirred suspension of methyltriphenylphosphonium bromide (0.565 g) in anhydrous ether (10 ml) to provide a yellow solution, to which was added a solution of the title compound of Preparation 14 (0.5 g) in anhydrous tetrahydrofuran (10ml). The reaction mixture was heated at 30° C. for 4 hours, allowed to cool and partitioned between ether (100 ml) and saturated aqueous sodium bicarbonate solution (100 ml). The organic phase was separated, dried and evaporated under reduced pressure, then the residue purified by column chromatography on silica gel, using hexane:dichloromethane (1:9) as eluant, to furnish the title compound as a white solid, m.p. 129–130° C. δ(CDCl3): 2.16 (s,3H), 5.29 (s,1H), 5.80 (s,1H), 7.59 (s,1H), 7.88 (s,2H). MS (thermospray): M/Z [M+NH$_4$] 362.9; C$_{14}$H$_8$Cl$_2$F$_3$N$_3$+NH$_4$ requires 363.04.

Preparation 16

3-Cyano-1-(2,6-dichloro-4-pentafluorothiophenyl)-4-(2-iodo-1-methoxyethyl)pyrazole Mercuric oxide (0.325 g) and iodine (0.381 g) were added to a stirred solution of the title compound of Preparation 8 (0.5 g) in methanol (10 ml), then the resulting mixture heated under reflux for 3 hours, allowed to cool and evaporated under reduced pressure. The residue was purified by column chromatography on silica gel, using dichloromethane as eluant, to afford the title compound as a yellow solid, m.p. 92–94° C. δ(CDCl$_3$): 3.46 (s,3H), 3.54 (m,2H), 4.49 (t,1H), 7.70 (s,1H), 7.78 (s,2H).

Preparation 17

3-Cyano-1-(2,6-dichloro-4-pentafluorothiophenyl)-4-(1-methoxyethenyl)-pyrazole 1,8-Diazabicyclo[5,4.0]undec-7-ene (0.064 g) was added to a stirred solution of the title compound of Preparation 16 (0.2 g) in toluene (10 ml). After 18 hours at room temperature, the reaction mixture was evaporated under reduced pressure and the residue purified by column chromatography on silica gel, using hexane and then hexane:dichloromethane (1:5) as eluants, to yield the title compound as a white solid, m.p. 116–118° C. δ(CDCl$_3$): 3.75 (s,3H), 4.45 (d,1H), 4.98 (d,1H), 7.78 (s,2H+1H). MS (thermospray): M/Z [M+H] 362.1; C$_{14}$H$_8$Cl$_2$F$_3$N$_3$O+H requires 362.01.

Preparation 18

N-[3-Cyano-1-(2,6-dichloro-4-trifluoromethylphenyl)pyrazole-4-ylmethylidene]-N'-(4-methylphenylsulphonyl) hydrazine, lithium salt A solution of the title compound of Preparation 9 (0.333 g) and p-toluenesulphonylhydrazine (0.186 g) in tetrahydrofuran was stirred at room temperature for 10 minutes and then activated 3 Å molecular sieves (2 pellets, ca. 0.011 g) were added. The mixture was cooled to −78° C. under nitrogen and a 2.5 M solution of n-butyllithium in hexane (0.4 ml) added over 3 minutes. The reaction mixture was allowed to warm to room temperature, filtered and the filtrate treated with hexane (40 ml). The resulting white precipitate was collected by filtration and dried to provide the title compound as a white solid. δ(DMSO d$_6$): 2.28 (s,3H), 7.10 (d,2H), 7.45 (s,1H), 7.68 (d,2H), 8.23 (s,1H), 8.28 (s, 2H). MS (thermospray): M/Z [M+H] 507.8; C$_{19}$H$_{11}$Cl$_2$F$_3$N$_5$O$_2$SLi+H requires 508.02.

Preparation 19

5-Amino-1-(2,6-dichloro-4-trifluoromethyphenyl)-3-methylpyrazole

3-Aminocrotononitrile (5.0 g) was added to a stirred solution of 2,6-dichloro-4-trifluoromethylphenylhydrazine (15.0 g) in ethanol (100 ml), then the resulting solution treated with concentrated sulphuric acid (1.0 ml) to produce a white solid precipitate. The mixture was heated under reflux for 6 hours, allowed to cool and stirred for a further 18 hours at room temperature; this cycle was repeated, then more concentrated sulphuric acid (4 ml) added. The reaction mixture was heated at 60° C. for 8 hours, allowed to cool, stirred at room temperature for 18 hours and evaporated under reduced pressure. The resulting orange oil was partitioned between dichloromethane (100 ml) and water (100 ml), then the organic phase dried, allowed to stand at room temperature for 18 hours and filtered to remove some white solid material. The filtrate was evaporated under reduced pressure to give an orange oil which was triturated with hot hexane. On cooling, the hexane solution deposited a yellow oil which slowly crystallised to furnish the title compound as a white solid, m.p. 80–83° C. Found: C, 42.73; H, 2.62; N, 13.58. C$_{11}$H$_8$Cl$_2$F$_3$N$_3$ requires 42.61; H, 2.60; N, 13.55%. δ(CDCl$_3$): 2.25 (s,3H), 3.48 (br.s,2H), 5.52 (s,1H), 7.70 (s,2H). MS (thermospray): M/Z [M] 310.0; C$_{11}$H$_8$Cl$_2$F$_3$N$_3$ requires 310.12.

Preparation 20

5-Amino-1-(2,6-dichloro-4-trifluoromethylphenyl)-4-iodo-3-methylpyrazole

N-Iodosuccinimide (5.5 g) was added to a stirred solution of the title compound of Preparation 19 (9.0 g) in acetonitrile (200 ml) at room temperature. The reaction mixture was heated under reflux for 1 hour, left at room temperature for 18 hours and then evaporated under reduced pressure. The residue was extracted with hot hexane and the precipitate obtained from the cool hexane solution was collected and dried to afford the title compound as an off-white solid, m.p. 116–118° C. δ(CDCl$_3$): 2.24 (s,3H), 3.68 (br.s,2H), 7.74 (s,2H). MS (thermospray): M/Z [M+H] 435.8; C$_{11}$H$_7$Cl$_2$F$_3$IN$_3$+H requires 435.91

Preparation 21

1(-2,6-Dichloro-4-trifluoromethylphenyl)-4-iodo-3-methylprazole t-Butyl nitrite (2.33 ml) was added dropwise to a stirred solution of the title compound of Preparation 20 (2.85 g) in tetrahydrofuran (35 ml) at 0° C. The reaction mixture was allowed to warm to room temperature, heated under reflux for 1.5 hours, then evaporated under reduced pressure. The residue was purified by column chromatography on silica gel, using hexane:dichloromethane (1:1) as eluant, to give a yellow oil which was further purified in similar fashion, using hexane:dichloromethane (2:1) as eluant. Thus was obtained the title compound as a white solid, m.p. 118.5–119.4° C. δ(CDCl$_3$): 2.18 (s,3H), 7.54 (s,1H), 7.70 (s,2H). MS (thermospray): M/Z (M+H] 420.5; C$_{11}$H$_6$Cl$_2$F$_3$IN$_2$+H requires 420.90.

Preparation 22

1-(2,6-Dichloro-4-trifluoromethylphenyl)-4-ethenyl-3-methylpyrazole

Tetrakis(triphenylphosphine)palladium(0) (0.1 g) and tri-n-butyl(vinyl)tin (2 ml) were added to a stirred solution of the title compound of Preparation 21 (2.06 g) in dimethylformamide (25 ml) and the reaction mixture heated at 70° C. for 2 hours, then evaporated under reduced pressure. The residue was partitioned between ether and water, the aqueous phase separated and extracted with ether (×2) and the combined organic solutions washed with brine, dried (Na$_2$SO$_4$) and evaporated under reduced pressure. The residue was purified by column chromatography on silica gel, using hexane:ether (9:1) as eluant, followed by reverse phase HPLC on C18 silica, using acetonitrile: water:methanol (40:50:10) as eluant, to yield the title compound as a white solid, m.p. 68.1–68.7° C. δ(CDCl$_3$): 2.44 (s,3H), 5.24 (d,1H), 5.50 (d,1H), 6.62 (dd,1H), 7.57 (s,1H), 7.74 (s,2H). MS (thermospray): M/Z [M+H] 321.1; C$_{13}$H$_9$Cl$_2$F$_3$N$_2$+H requires 321.02.

Preparation 23

1-(2,6-Dichloro-4-trifluoromethylphenyl)-3,5-dimethylpyrazole

Pentan-2,4-dione (0.100 g) was added to a stirred solution of 2,6-dichloro-4-trifluoromethylphenylhydrazine (0.245 g) in ethanol (4.5 ml), followed by glacial acetic acid (0.5 ml), at room temperature. The reaction mixture was heated under reflux for 1 hour, then evaporated under reduced pressure. The residue was purified by column chromatography on silica gel, using dichloromethane as eluant, to provide a colourless oil initially which crystallised, after removal of extraneous solvent in vacuo, to furnish the title compound (0.265 g), m.p. 87–89° C. δ(CDCl$_3$): 2.10 (s,3H), 2.32 (s,3H), 6.07 (s,1H), 7.72 (s,2H). MS (thermospray): M/Z [M] 309.0; C$_{12}$H$_9$Cl$_2$F$_3$N$_2$ requires 309.12.

Preparation 24

1-(2,6-Dichloro-4-trifluoromethylphenyl)-3,5-dimethyl-4-iodopyrazole

A solution of N-iodosuccinimide (0.158 g) in acetonitrile (3 ml) was added dropwise to a stirred solution of the title compound of Preparation 23 (0.218 g) in acetonitrile (3 ml) at room temperature. After a further 27 hours, the reaction mixture was evaporated under reduced pressure and the residue purified by column chromatography on silica gel (5 g), using dichloromethane as eluant, to afford the title compound as a yellow oil. δ(CDCl$_3$): 2.11 (s,3H), 2.32 (s,3H), 7.73 (s,2H). MS (thermospray): M/Z [M+H] 435.0; C$_{12}$H$_8$ Cl$_2$F$_3$IN$_2$+H requires 434.91.

Preparation 25

1-(2,6-Dichloro-4-trifluoromethylphenyl)-3,5-dimethyl-4-ethenylpyrazole

A solution of the title compound of Preparation 24 (1.0 g), tri-n-butyl(vinyl)-tin (2 ml) and tetrakis (triphenylphosphine)palladium(0) (0.1 g) in dimethylformamlde (10 ml) was stirred at 75° C. for 2 hours and then at room temperature for 18 hours. The reaction mixture was sequentially stirred at 75° C. for 2 hours, treated with tri-n-butyl(vinyl)tin (2 ml), stirred at 75° C. for 2 hours, treated with tetrakis(triphenylphosphine)palladium(0) (0.1 g), stirred at 75° C. for 2 hours and evaporated under reduced pressure. The residue was partitioned between dichloromethane and water, then the organic phase separated, washed successively with water (×2) and brine, dried (Na$_2$SO$_4$) and evaporated under reduced pressure. The resulting crude product was adsorbed onto silica gel (20 g) and then purified by column chromatography on silica gel (150 g), using an elution gradient of hexane:dichloromethane (100:0 to 0:100), to give the title compound as a yellow oil. δ(CDCl$_3$): 2.11 (s,3H), 2.40 (s,3H), 5.23 (d,1H), 5.41 (d,1H), 6.59 (dd,1H), 7.71 (s,2H). MS (thermospray): M/Z [M+H] 335.1; C$_{14}$H$_{11}$Cl$_2$F$_3$N$_2$+H requires 335.03.

Preparation 26

5-Amino-4-iodo-3-methyl-1-(2,4,6-trichlorophenyl) pyrazole

A stirred solution of 5-amino-3-methyl-1-(2,4,6-trichlorophenyl)pyrazole (WO-A-94/13643; 35 g) and N-iodosuccinimlde (29 g) in acetonitrile (450 ml) was heated under reflux for 1.5 hours, then the reaction mixture allowed to cool and evaporated under reduced pressure. The residue was dissolved in dichloromethane and the solution washed successively with aqueous sodium thiosulphate solution, water and brine, then dried (Na$_2$SO$_4$) and evaporated under reduced pressure. The resulting dark coloured solid was triturated with hexane to yield the title compound as a pale orange solid, m.p. 135–137° C. δ(CDCl$_3$): 2.25 (s,3H), 3.67 (br.s,2H), 7.49 (s,2H). MS (thermospray): M/Z [M+H] 401.4; C$_{10}$H$_7$Cl$_3$IN$_3$+H requires 401.88.

Preparation 27

4-Iodo-3-methyl-1-(2,4,6-trichlorophenyl)pyrazole

A solution of t-butyl nitrite (12 ml) in anhydrous tetrahydrofuran (50 ml) was added dropwise to a stirred, gently refluxing solution of the title compound of Preparation 26 (18.11 g) in anhydrous tetrahydrofuran (120 ml). The reaction mixture was allowed to cool and evaporated under reduced pressure, then the residue purified by column chromatography on silica gel, using hexane followed by hexane:ethyl acetate (19:1) as eluants, to provide the title compound as an orange solid, m.p. 97–99° C. $\delta(CDCl_3)$: 2.36 (s,3H), 7.47 (s,2H), 7.48 (s,1H) MS (thermospray): M/Z [M+H] 386.9; $C_{10}H_6Cl_3IN_2$+H requires 386.87.

Preparation 28

4-Ethenyl-3-methyl-1-(2,4,6-trichlorophenyl) pyrazole

A stirred solution of the title compound of Preparation 27 (16.62 g), tri-n-butyl(vinyl)tin (27.27 g) and tetrakis (triphenylphosphine)palladium(0) (0.6 g) in anhydrous dimethyiformamlde (100 ml) was heated at 75° C. for 2.5 hours. More tetrakis(triphenylphosphine)palladium(0) (0.6 g) was added and the reaction mixture heated at 75° C. for a further 2 hours, then evaporated under reduced pressure. The residue was purified by column chromatography on silica gel, using hexane and then hexane:ethyl acetate (99:1) as eluants, to furnish the title compound as a pale yellow solid, m.p. 71–73° C. $\delta(CDCl_3)$: 2.40 (s,3H), 5.19 (d,1H), 5.49 (d,1H), 6.59 (dd,1H), 7.47 (s,2H), 7.50 (s,1H). MS (thermospray): M/Z [M+NH$_4$] 287.0; $C_{12}H_9Cl_3N_2$+NH$_4$ requires 286.99.

Preparation 29

3-Cyano-1-(2,6-dichloro-4-trifluoromethylphenyl)-4-trifluoroacetylpyrazole t-Butyl nitrite (12.45 ml) was added dropwise to a stirred solution of 5- amino-3-cyano-1-(2,6-dichloro-4-trifluoromethylphenyl)-4-trifluoroacetylpyrazole (JP-A-8-311036; 30 g) in tetrahydrofuran (250 ml) and the mixture stirred at 55° C. for 16 hours. Further quantities of t-butyl nitrite added/subsequent periods of stirring at 55° C. were as follows: 9 ml/7 hours, 6 ml/16 hours, 9 ml/6 hours, 4.75 ml/16 hours, 6 ml/6 hours and 3.5 ml/22 hours. The reaction mixture was allowed to cool and evaporated under reduced pressure, then the residue combined with those obtained from three identical preparations. Purification by column chromatography on silica gel (1 Kg), using hexane:dichloromethane (6:4) and then dichloromethane as eluants, gave a yellow oil which, on trituration with hexane (3×50 ml) followed by dichloromethane (100 ml), provided the title compound as a white solid, m.p. 124–125° C. $\delta(CDCl_3)$: 7.83 (s,2H), 8.30 (s,1H). MS (thermospray): M/Z [M+H] 401.7; $C_{13}H_3Cl_2F6N_3O$+H requires 401.96.

Preparation 30

3-Cyano-1-(2,6-dichloro-4-trifluoromethylphenyl)-4-(3,3,3-trifluoropropen-2-yl)pyrazole A 2.5M solution of n-butyllithium in hexane (0.1 ml) was added dropwise to a stirred suspension of methyltriphenylphosphonium iodide (111 mg) in tetrahydrofuran (6 ml) under nitrogen at room temperature. The resulting reddish brown solution was added dropwise, under nitrogen, to a stirred solution of the title compound of Preparation 29 (100 mg) in tetrahydrofuran (1 ml) at room temperature and the reaction mixture stirred for 30 minutes. Water (30 ml) was then added, extraction with ether (50 ml) effected and the organic extract dried (Na$_2$SO$_4$) and evaporated under reduced pressure. The residue was purified by column chromatography on silica gel (10 g), using hexane:dichloromethane (1:1) as eluant, to yield the title compound as a white solid. m.p. 103–104° C. $\delta(CDCl_3)$: 6.20 (s,1H), 6.39 (s,1H), 7.78 (s,1H), 7.80 (s,2H). MS (thermospray): M/Z [M+H] 399.8; $C_{14}H_5Cl_2F_6N_3$+H requires 400.0.

Preparation 31

3-Cyano-1-(2,6-dichloro-4-trifluoromethylphenyl)-4-(3-trifluoromethyl-1-pyrazolin-3-yl)pyrazole A solution of diazomethane (40 mmol) in ether (100 ml) was added slowly to a stirred solution of the title compound of Preparation 30 (27 g) in ether (150 ml) at room temperature and the mixture stirred for 40 minutes. More diazomethane (50 mmol) in ether (150 ml) was slowly added and the reaction mixture stirred for a further 16 hours at room temperature. The excess diazomethane was distilled off, then the solvent evaporated under reduced pressure to provide the title compound as a white solid. $\delta(CDCl_3)$: 2.23 (m,1H), 2.52 (m,1H), 4.90 (m,2H), 7.78 (s,2H), 8.15 (s,1H). MS (thermospray): M/Z [M+NH$_4$] 458.8; $C_{15}H_7Cl_2F_6N_5$+NH$_4$ requires 459.0.

Preparation 32

5-Chloro-3-cyano-1-(2,6-dichlorontrifluoromethylphenyl)-4-iodopyrazole

A ca. 1M solution of nitrosyl chloride in dichloromethane (2.7 ml) was added dropwise to a stirred, ice-cooled solution of the title compound of Preparation 1 (1.0 g) in acetonitrile (15 ml), then the reaction mixture heated under reflux for 10 minutes and evaporated under reduced pressure. The residue was purified by column chromatography on silica gel, using hexane:toluene (2:1) and then toluene as eluants, to give the title compound as a pale orange solid, m.p. 115.7–116.3° C. $\delta(CDCl_3)$: 7.80 (s,2H). MS (thermospray): M/Z [M+] 466.0; $C_{11}H_2Cl_3F_3IN_3$+H requires 465.84.

Preparation 33

5-Chloro-3-cyano-1-(2,6-dichloro-4-trifluoromethylphenyl)-4-ethenylpyrazole

Tetrakis(triphenylphosphine)palladium (0) (0.448 g) was added to a stirred solution of the title compound of Preparation 32 (6.0 g) in dimethylformamlde (75 ml) at room temperature followed, 5 minutes later, by the dropwise addition of tri-n-butyl(vinyl)tin (11.3 ml). The resulting mixture was heated at 70° C. for 18 hours, then evaporated under reduced pressure and the residue partitioned between ether and water. The organic phase was separated, dried and evaporated under reduced pressure, then the resulting residue purified by column chromatography on silica gel, using hexane and then hexane:dichloromethane (2:1) as eluants, followed by crystallisation from hexane, to yield the title compound as a white solid, m.p. 69.8–70.4° C. $\delta(CDCl_3)$: 5.61 (d,1H), 6.20 (d,1H), 6.56 (dd,1H), 7.80 (s,2H). MS (thermospray): M/Z [M+NH$_4$] 383.1; $C_{13}H_5Cl_3F_3N_3$+NH$_4$ requires 382.98.

Preparation 34

5-Amino-1-(2,6-dichloro-4-trifluoromethylphenyl)-4-iodo-3-trifluoromethylpyrazole Obtained from 5-amino-1-(2,6-dichloro-4-trifluoromethylphenyl)-3-trifluoromethylpyrazole (WO-A-

87/03781), by analogy with Preparation 1, as an off-white solid, m.p. 126° C. δ(CDCl$_3$): 3.90 (br.s,2H), 7.80 (s,2H). MS (thermospray): M/Z [M+H] 490.2; C$_{11}$H$_4$Cl$_2$F$_6$IN$_3$+H requires 489.88.

Preparation 35

1-(2,6-Dichloro-4-trifluoromethylphenyl)-4-iodo-3-trifluoromethylpyrazole

Obtained from the title compound of Preparation 34, by analogy with Preparation 3, as an oil which solidified on standing. Crystallisation from propan-2-ol provided the title compound as a yellow solid, m.p. 109–112° C. Found: C,27.87; H,0.69; N,6.15. C$_{11}$H$_4$Cl$_2$F$_6$IN$_3$ requires C,27.82; H,0.64; N,5.90%. δ(CDCl$_3$): 7.70 (s,1H); 7.77 (s,2H).

Preparation 36

1-(2,6-Dichloro-4-trifluoromethylphenyl)-4ethenyl-3-trifluoromethylpyrazole

Obtained from the title compound of Preparation 35, by analogy with Preparation 4, except that the crude product was crystallised from hexane and then further purified by column chromatography on silica gel, using ether as eluant, followed by reverse phase HPLC on C18 silica, using acetonitrile:methanol:water (40:10:50) as eluant, followed by crystallisation from propan-2-ol, to furnish the title compound as a pale yellow solid, m.p. 95–98° C. δ(CDCl$_3$): 5.39 (d,1H), 5.65 (d,1H), 6.69 (dd,1H), 7.80 (s,1H), 7.81 (s,2H). MS (thermospray): M/Z [M+NH$_4$] 391.9; C$_{13}$H$_6$Cl$_2$F$_6$N$_2$+NH$_4$ requires 392.02.

Preparation 37

5-Amino-1-(2,6-dichloro-4-trifluoromethylphenyl)-3-phenylpyrazole

A solution of 2,6-dichloro-4-trifluoromethylphenylhydrazine (0.2459 g) in ethanol (2 ml) was added to a stirred solution of benzoylacetonitrile (0.145 g) in ethanol (8 ml) and the resulting solution heated under reflux for 6 hours. Glacial acetic acid (1 ml) was added and the resulting mixture heated under reflux for a further 6 hours and then evaporated under reduced pressure. The residue was purified by column chromatography on silica gel (10 g), using dichloromethane as eluant, followed by reverse phase HPLC on C18 silica, using acetonitrile:methanol:water (50:10:40) as eluant, to afford the title compound as a white solid, m.p. 141.5–142.5° C. δ(CDCl$_3$): 3.60 (br.s,2H), 6.08 (s,1H), 7.30–7.45 (m,3H), 7.80 (s,2H), 7.80–7.85 (m,2H). MS (thermospray): M/Z [M+H] 372.1; C$_{16}$H$_{10}$Cl$_2$F$_3$N$_2$+H requires 372.03.

Preparation 38

5-Amino-1-(2,6-dichloro-4-triflucromethylphenyl)-4-iodo-3-phenylkyrazole

Obtained from the title compound of Preparation 37, by analogy with Preparation 1 except that the reaction mixture was stirred for 18 hours, as a yellow solid, m.p. 162–164° C. δ(CDCl$_3$): 3.80 (br.s,2H), 7.35 (m,3H), 7.78 (s,2H), 7.95 (m,2H). MS (thermospray): M/Z [M+H] 498.1; C$_{16}$H$_9$Cl$_2$F$_3$IN$_3$+H requires 497.93.

Preparation 39

1-(2,6-Dichloro-4-trifluoromethylphenyl)-4iodo-3-phenylpyrazole

A solution of t-butyl nitrite (3.0 g) in tetrahydrofuran (20 ml) was added dropwise over 30 minutes to a stirred solution of the title compound of Preparation 38 (2.5 g) in tetrahydrofuran (50 ml) at 65° C. After a further 3 hours at 65° C. the reaction mixture was allowed to cool, kept at room temperature for 18 hours and then evaporated under reduced pressure. The resulting oil was purified by two column chromatography operations on silica gel, firstly using dichloromethane as eluant and then, sequentially, hexane, hexane:ethyl acetate (95:5) and hexane:ethyl acetate (90:10) as eluants, to give the title compound as a cream solid, m.p. 88–89° C. δ(CDCl$_3$): 7.45 (m,3H), 7.70 (s, 1H), 7.72 (s,2H), 7.95 (m,2H). MS (thermospray): M/Z [M+H] 482.8; C$_{16}$H8Cl$_2$F$_3$IN$_2$+NH requires 482.91.

Preparation 40

1-(2,6-Dichloro-4-trifluoromethylphenyl)-4-ethenyl-3-phenylpyrazole

Tetrakis(triphenylphosphine)palladium(0) (0.07 g) was added to a stirred solution of the title compound of Preparation 39 (1.0 g) in dimethylformamlde (12 ml) at room temperature followed, 10 minutes later, by tri-n-butyl(vinyl) tin (1.8 ml). The resulting mixture was heated at 70° C. for 6 hours, allowed to stand at room temperature for 18 hours, then evaporated under reduced pressure. The residue was partitioned between dichloromethane (50 ml) and water (50 ml), then the organic phase separated, dried (MgSO$_4$) and evaporated under reduced pressure. The residue was purified by two column chromatography operations on silica gel, firstly using an elution gradient of ethyl acetate in hexane and secondly using an elution gradient of ether in hexane, to yield the title compound as a yellow oil. δ(CDCl$_3$): 5.25 (d, 1 H), 5.65 (d, 1H), 6.80 (dd, 1H), 7.45 (m,3H), 7.75 (m,5H). MS (thermospray): M/Z [M+H] 383.3: C$_{18}$H$_{11}$ Cl$_2$F$_3$N$_2$+H requires 383.03.

Preparation 41

5-Amino-4-chlorodifluoroacetyl-3-cyano-1-(2,6-dichloro-4-trifluoromethylphenyl)pyrazole Chlorodifluoroacetic anhydride (30.37 g) was added dropwise to a stirred, ice-cooled solution of 5-amino-3-cyano-1-(2,6-dichloro-4-trifluoromethylphenyl)pyrazole (EP-A-0295117; 20.0 g) in pyridine (200 ml), then the reaction mixture stirred at room temperature for 16 hours. The resulting mixture was concentrated by removal of pyridine (150 ml) under reduced pressure, then poured into stirred ice/water (500 ml). The pH of this mixture was adjusted to 1 by the dropwise addition of concentrated hydrochloric acid (30 ml), with stirring, and extraction with ethyl acetate (2×500ml) effected. The conbined organic extracts were washed with saturated aqueous sodium bicarbonate solution (500 ml), dried (MgSO$_4$) and evaporated under reduced pressure, The residue was dissolved in a mixture of tetrahydrofuran (200 ml) and water (50 ml), then the solution heated at 60° C. for 16 hours, allowed to cool and the bulk of the tetrahydrofuran removed by evaporation under reduced pressure. Extraction with ethyl acetate (2×300 ml) was effected, then the combined organic extracts washed sequentially with water (100 ml) and brine (2×100 ml), dried (MgSO$_4$) and evaporated under reduced pressure. The resulting residue was crystallised from propan-2-ol to provide the title compound as a white solid, m.p. 225–226° C. δ(CDCl$_3$): 6.08 (br.s,2H), 7.84 (s,2H). MS (thermospray): M/Z [M+NH$_4$] 450.1; C$_{13}$H$_4$Cl$_3$F$_5$N$_4$O+NH$_4$ requires 450.0.

Preparation 42

4-Chlorodifluoroacetyl-3-cyano-1-(2,6-dichloro-4-trifluoromethylphenyl)pyrazole t-Butyl nitrite (12.45 ml) was added dropwise to a stirred solution of the title compound of Preparation 41 (13.7 g) in tetrahydrofuran (100 ml) and the mixture heated at 60° C. for 22 hours, allowed to cool and evaporated under reduced pressure. The residue was purified by column chromatography on silica gel (50 g), using dichloromethane as eluant, followed by trituration with hexane (5×50 ml) and crystallisation from dichloromethane, to furnish the title compound as a white solid, m.p. 124–125° C. δ(CDCl$_3$): 7.83 (s,2H), 8.27 (s,1H). MS (thermospray): M/Z [M+NH$_4$]435.2; C$_{13}$H$_3$Cl$_3$F$_5$N$_3$O+NH$_4$ requires 435.0.

Preparation 43

4-(3-Chloro-3,3-difluoropropen-2-yl)-3-cyano-l-(2.6-dichloro-4-trifluoromethylphenyl)pyrazole A 2.5 M solution of n-butyllithium in hexane (3.8 ml) was added dropwise to a stirred suspension of methyltriphenylphosphonium iodide (3.817 g) in tetrahydrofuran (20 ml) under nitrogen at room temperature. The resulting reddish brown solution was added dropwise, under nitrogen, to a stirred solution of the title compound of Preparation 42 (3.95 g) in tetrahydrofuran (30 ml) at room temperature and the reaction mixture stirred for 1 hour. Water (50 ml) was then added, extraction with ether (2×50 ml) effected and the combined organic extracts dried (Na$_2$SO$_4$) and evaporated under reduced pressure. The residue was purified by column chromatography on silica gel (100 g), using hexane:dichloromethane (1:1) as eluant, followed by crystallisation from propan-2-ol, to afford the title compound as a white solid. m.p. 113–114° C. δ(CDCl$_3$): 6.12 (s,1H), 6.20 (s,1H), 7.75 (s,2H), 7.80 s, 1H). MS (thermospray): M/Z [M+NH$_4$] 433.0; C$_{14}$H$_5$Cl$_3$F$_5$N$_3$+NH$_4$ requires 433.0.

Preparation 44

4-(3-Chlorodifluoromethyl-1-pyrazolin-3-yl)-3-cyano-1-(2,6-dichloro-4-trifluoromethylphenyl)pyrazole A solution of diazomethane in ether (7.0 ml, 2.3 mmol) was added slowly to a stirred solution of the title compound of Preparation 43 (800 mg) in ether (10 ml) at room temperature and the mixture stirred for 1 hour. The excess diazomethane and solvent were evaporated under a steady stream of nitrogen to give the title compound as a white solid. δ(CDCl$_3$): 2.27 (m,1H), 2.58 (m,1H), 4.90 (m,2H), 7.75 (s,2H), 8.06 (s,1H). MS (thermospray): M/Z [M+NH$_4$] 474.8; C$_{15}$H$_7$Cl$_3$F$_5$N$_5$+NH$_4$ requires 475.0.

Preparation 45

5-Amino-3-cyano-1-(2,6-dichloro-4-trifluoromethylphenyl)-4-propanoylpyrazole p-Toluenesulphonic acid monohydrate (2.92 g) was added to a stirred solution of 5-amino-3-cyano-1-(2,6-dichloro-4-trifluoromethylphenyl)-4-(prop-1-yn-l-yl)pyrazole (WO-A-97107102; 2.1g) in acetonitrle (40 ml) and the mixture stirred at room temperature for 1 hour. Further p-toluenesulphonic acid monohydrate (1.0) was added and this mixture stirred at room temperature for 16 hours. Further acetonitrile (20 ml) and yet more p-toluenesulphonic acid monohydrate (1.0 g) were added and stirring continued for 1 hour, then the reaction mixture was poured into saturated aqueous sodium bicarbonate solution (500 ml) and extracted with ether (2×100 ml). The combined organic extracts were washed with brine (100 ml), dried (Na$_2$SO$_4$) and evaporated under reduced pressure, then the residue purified by column chromatography on silica gel (70 g), using dichloromethane as eluant, to yield the title compound as a pale brown solid, m.p. 167–169° C. δ(CDCl$_3$): 1.26 (t,3H), 3.03 (q,2H), 5.83 (br.s,2H), 7.80 (s,2H). MS (thermospray): M/Z [M+H] 377.2; C$_{14}$H$_9$Cl$_2$F$_3$N$_4$O+H requires 377.0.

Preparation 46

3-Cyano-1-(2,6-dichloro-4-trifluoromethylphenyl4-propanoylpyrazole t-Butyl nitrite (0.66 ml) was added dropwise to a stirred solution of the title compound of Preparation 45 (1.2 g) in tetrahydrofuran (30 ml) and the mixture stirred at room temperature for 1 hour. Further t-butyl nitrite (0.3 ml) was added and the mixture stirred at room temperature for 1 hour. Next, the reaction mixture was heated at 60° C. for 10 minutes, allowed to cool and evaporated under reduced pressure. The residue was purified by column chromatography on silica gel (50 g), using dichioromethane as eluant, to provide the title compound as a very pale yellow solid, m.p. 143° C. δ(CDCl$_3$): 1.28 (m,3H), 3.01 (q,2H), 7.80 (s,2H), 8.15 (s,1H). MS (thermospray): M/Z [M+NH$_4$] 379.3; C$_{14}$H$_8$Cl$_2$F$_3$N$_3$O+NH$_4$ requires 379.0.

Preparation 47

4-But-l-en-2-yl)-3-cyano-1-(2,6-dichloro-4-trifluoromethylphenyl)pyrazole

Obtained from the title compound of Preparation 46, by analogy with Preparation 43 but using hexane:dichloromethane (2:3) as chromatographic eluant and no subsequent crystallisation, as a white solid, m.p. 104–105° C. δ(CDCl$_3$): 1.19 (t,3H), 2.47 (q,2H), 5.29 (s,1H), 5.74 (s,1H), 7.60 (s,2).7.79 (s,2H). MS (electrospray): M/Z [M+H] 360.1; C$_{15}$H$_{10}$Cl$_2$F$_3$N$_3$+H requires 360.

Preparation 48

3-Cyano-1-(2,6-dichloro-4-trifluoromethylphenyl)-4-pentafluoropropanoylpyrazole

A 2.5 M solution of n-butyllithium in hexane (2.78 ml) was added to a stirred solution of the title compound of Preparation 3 (3.0 g) in tetrahydrofuran (80 ml) at −80° C. under nitrogen, at such a rate that the temperature of the reaction mixture did not exceed −73° C. The mixture was stirred at −73° C. for 10 minutes and then a solution of methyl pentafluoropropionate (0.89 ml) in tetrahydrofuran (5 ml) was added at such a rate that the temperature of the reaction mixture did not exceed −75° C. Upon completion of the addition, the mixture was allowed to warm to room temperature over a period of 1.5 hours, then water (100 ml) added and the resulting mixture extracted with ethyl acetate (2×80 ml). The combined organic layers were dried (Na$_2$SO$_4$) and evaporated under reduced pressure, then the residue purified by column chromatography on silica gel (1 50 g), using hexane:dichloromethane (1:9) as eluant, and further purified by column chromatography on silica gel (50 g), using hexane:ether (9:1) as eluant, to furnish the title compound as a white solid, m.p. 120° C. δ(CDCl$_3$): 7.80 (s,2H), 8.25 (s,1H). MS (thermospray): M/Z [M+NH$_4$] 468.9; C$_{14}$H$_3$Cl$_2$F$_8$N$_3$O+NH$_4$ requires 469.0.

Preparation 49

3-Cyano-1-(2,6-dichloro-4-trifluoromethylphenyl)-4-(3,3,4,4,4-pentafluorobut-1-en-2-yl)pyrazole Obtained from the title compound of Preparation 48, by analogy with Preparation 43 but without any post-chromatographic crystallisation, as a white solid, m.p. 107–108° C. δ(CDCl$_3$): 6.23 (s,1H), 6.43 (s,1H), 7.73 (s,1H), 7.79 (s,2H). MS (electrospray): M/Z [M+H] 450.0; C$_{15}$H$_5$Cl$_2$F$_8$N$_3$+H requires 450.0.

Preparation 50

3-Cyano-1-(2,6-dichloro-4-trifluoromethylphenyl)-4-(3-pentafluoroethyl-1-pyrazolin-3-yl)pyrazole Obtained from the title compound of Preparation 49, by analogy with Preparation 44, as a white solid. δ(CDCl$_3$): 2.26 (m,1H), 2.61 (m,1H), 4.83 (m,2H), 7.76 (s,2H), 7.98 (s,1H). MS (thermospray): M/Z [M+H] 491.8; C$_{16}$H$_7$Cl$_2$F$_8$N$_5$+H requires 492.0.

Preparation 51

3-Cyano-1-(2,6-dichloro-4-trifluoromethylphenyl)-4-heptafluorobutanoylpyrazole

Obtained from the title compound of Preparation 3 and methyl heptafluorobutyrate, by analogy with Preparation 48 but using hexane:ether (2:3) as eluant in the first chromatographic purification step and an elution gradient of hexane:ether (19:1 to 9:1) in the second such step, as a pale yellow solid, m.p. 102–103° C. δ(CDCl$_3$): 7.80 (s,2H), 8.24 (s,1H),. MS (thermospray): M/Z [M+NH$_4$] 518.7; C$_{15}$H$_3$Cl$_2$F$_{10}$N$_3$O+NH$_4$ requires 519.0.

Preparation 52

3-Cyano-1-(2,6dichloro-4-trifluoromethylphenyl)-4-(3,3,4,4,5,5,5-heptafluoropent-1-en-2-yl)pyrazole Obtained from the title compound of Preparation 51, by analogy with Preparation 43 but using dichloromethane as eluant in a first chromatographic purification step and hexane:dichloromethane (1:1) as eluant in a second such step, with no subsequent crystallisation, as a white solid, m.p. 109–110° C. δ(CDCl$_3$): 6.24 (s,1H), 6.43 (s,1H) 7.73 (s, 1H), 7.80 (s,2H). MS (electrospray): M/Z [M+H] 500.0; C$_{16}$H$_5$Cl$_2$F$_{10}$N$_3$+NH requires 500.0.

Preparation 53

3-Cyano-1-(2,6-dichloro-4-trifluoromethylphenyl)-4-(3-heptafluoropropyl-1-pyrazolin-3-yl)pyrazole Obtained from the title compound of Preparation 52, by analogy with preparation 44, as a white solid. δ(CDCl$_3$): 2.36 (m,1H), 2.58 (m,1H), 4.80 (m,1H), 4.87 (m,1H), 7.77 (s,2H), 7.98 (s,1 H). MS (thermospray): M/Z [M+NH$_4$] 559.3; C$_{17}$H$_7$Cl$_2$F$_{10}$N$_5$+NH$_4$ requires 559.0.

Preparation 54

5-Amino-3-cyano-1-(2,6-dichloro-4-trifluoromethylphenyl)-4 (3,3,3-trifluoropropen-2-yl) pyrazole A solution of 3,3,3-trifluoropropen-2-yl zinc bromide:N,N,N',N'-tetramethylethylenediamine complex in tetrahydrofuran (J. Org. Chem., 1991, 56, 7336; 4.5 ml, 5 mmol) was added to a stirred solution of the title compound of Preparation 1 (1.0 g) and tetrakis(triphenylphosphine)palladium (0) (60 mg) in anhydrous tetrahydrofuran (1.0 ml), under nitrogen, and the reaction mixture heated at 55° C. for 20 hours, allowed to cool and poured into stirred hexane (50 ml). The resulting mixture was filtered, the filter pad washed with ether (50ml) and the combined organic solutions evaporated under reduced pressure. The residue was purified by two column chromatography operations on silica gel (40 g, then 10 g), firstly using hexane:ether:dichloromethane (4:1:1) as eluant then, sequentially, hexane, hexane:ether (4:1) and hexane:ether:dichloromethane (4:1:1) as eluants, to afford the title compound as a very pale yellow solid, m.p. 147–148° C. δ(CDCl$_3$): 3.93 (br.s,2H), 5.96 (s,1H), 6.24 (s, 1H), 7.78(s,2H). MS (thermospray): M/Z [M+] 415.0; C$_{14}$H$_6$Cl$_2$F$_6$N$_4$+H requires 415.0.

Preparation 55

5-Amino-3-cyano-1-(2,6dichloro-4-trifluoromethylphenyl)-4-(3-trifluoromethyl-1-pyrazolin-3-yl)pyrazole Obtained from the title compound of Preparation 54, by analogy with Preparation 44, as a white solid. δ(CDCl$_3$): 2.28 (m, 1H), 2.60 (m, 1H), 4.77 (br.s,2H), 4.77 (m,1H), 5.02 (m,$_1$H), 7.78 (s,1H), 7.82 (s,1H). MS (thermospray): M/Z [M+H] 457.0; C$_{15}$H$_8$Cl$_2$F$_6$N$_6$+H requires 457.0.

Preparation 56

5-Amino-1-(3-chloro-5-trifluoromethyl)pyridin-2-yl-3-cyano-4-iodopyrazole

N-Iodosuccinimlde (10 g) was added to a stirred solution of 5-amino-1-[(3-chloro-5-trifluoromethyl) pyridin-2yl]-3-cyanopyrazole (EP-A-0500209; 7.91 g) in acetonitrile (100 ml) at room temperature. After 16 hours, the reaction mixture was evaporated under reduced pressure, the residual solid dissolved in dichloromethane and the resulting solution washed successively with aqueous sodium thiosulphate solution (×2), water and saturated brine, dried (MgSO$_4$) and evaporated under reduced pressure to give the title compound as a pink solid, m.p. 107–108° C. δ(CDCl$_3$) 5.15 (br.s,2H), 8.20 (s,1H), 8.67 (s,1H). MS (thermospray): M/Z [M+H] 413.1; C$_{10}$H$_4$ClF$_3$IN$_5$+H requires 412.9.

Preparation 57

1-[(3-Chloro-5-trifluoromethyl)pyridin-2-yl] -3-cyano-4-iodopyrazole

A solution of t-butyl nitrite (7.2 ml) in tetrahydrofuran (30 ml) was added dropwise to a stirred mixture of the title compound of Preparation 56 (12.5 g) in tetrahydrofuran (90 ml) gently heated to reflux, then the reaction mixture allowed to cool to room temperature and evaporated under reduced pressure. The residue was purified by column chromatography on silica gel, using hexane:ethyl acetate (4:1) as eluant, to yield the title compound as a yellow solid, m.p. 104–107° C. δ(CDCl$_3$): 8.20 (s,1H), 8.70 (s,1H). MS (thermospray): M/Z [M+H] 397.8; C$_{10}$H$_3$ClF$_3$IN$_4$+H requires 397.9.

Preparation 58

1-[(3-Chloro-5-trifluoromethyl)pyridin-2-yl] -3-cyano-4-ethenylpyrazole

Tri-n-butyl(vinyl)tin (9.19 g) and tetrakis (triphenylphosphine)palladium(0) (0.3 g) were added to a stirred solution of the title compound of Preparation 57 (10.50 g) in dimethylformamlde (100 ml) at room temperature, under nitrogen, and the resulting mixture heated at 75° C. for 16 hours, then allowed to cool. The mixture was evaporated under reduced pressure, the residue partitioned between dichloromethane and water, then the separated organic phase washed successively with water (×3) and saturated brine, dried (MgSO$_4$) and evaporated under reduced pressure. The residue was purified by column chromatography on silica gel, using hexane:ethyl acetate (9:1) as eluant, to provide the title compound as a white solid, m.p. 57.5–58.5° C. δ(CDCl$_3$): 5.50 (d,1H), 5.97 (d,1H), 6.65 (dd,1H), 8.20 (s,1H), 8.35 (s,1H), 8.70 (s,1H). MS (thermospray): M/Z [M+H] 297.9; C$_{12}$H$_6$ClF$_3$N$_4$+H requires 298.0.

Preparation 59

5-Amino-3-cyano-4-iodo-1-(2,4,6-trichlorophenyl)pyrazole

N-Iodosuccinimide (17.67 g) was added portionwise to a stirred solution of 5-amino-3-cyano-1-(2,4,6-trichlorophenyl)pyrazole (U.S. Pat. No. 5,232,940; 22.5 g) in acetonitrile (300 ml) and the resulting mixture stirred at room temperature for 1 hour, then evaporated under reduced pressure. The residue was partially purified by chromatography on silica gel (800 g), using an elution gradient of dichloromethane:ethyl acetate (100:0 to 0:100), to produce a pale brown solid which was further purified as follows. Trituration with hexane (25 ml) provided a residue which was dissolved in dichloromethane (500 ml). This solution was washed with water (500 ml), the aqueous washing back-washed with ethyl acetate (500 ml) and the combined organic solutions dried (Na$_2$SO$_4$) and evaporated under reduced pressure to furnish the title compound as a pale brown solid. δ(DMSO$_{d6}$): 6.28 (br.s,2H), 7.98 (s,2H). MS (thermospray): M/Z [M+H] 413.0; C$_{10}$H$_4$Cl$_3$IN$_4$+H requires 412.9.

Preparation 60

3-Cyano-4-iodo-1-(2,4,6-trichlorophenyl)pyrazole t-Butyl nitrite (7.13 ml) was added dropwise over 5 minutes to a stirred solution of the title compound of Preparation 59 (15.5 g) in tetrahydrofuran (400 ml), then the mixture stirred at room temperature for 1 hour, warmed to 60° C. over 40 minutes, allowed to cool and evaporated under reduced pressure. The resulting pale red solid was purified by column chromatography on silica gel (500 g), using dichloromethane as eluant, to afford the title compound as a very pale yellow solid. δ(CDCl$_3$): 7.52 (s,2H), 7.67 (s,1H). MS (thermospray): M/Z [M+NH$_4$] 414.8; C$_{10}$H$_3$Cl$_3$IN$_3$+NH$_4$ requires 414.9.

Preparation 61

3-Cyano-4-ethenyl-1-(2,4,6-trichlorophenyl)pyrazole

A mixture of the title compound of Preparation 60 (10.8 g), tri-n-butyl(vinyl)tin (20 ml), tetrakis(triphenylphosphine)palladium(0) (1.0 g) and dimethylformamlde (60 ml) was stirred at 75° C. for 3 hours, allowed to cool and poured into stirred water (100 ml). The resulting mixture was extracted with ether (2×150 ml) and the combined extracts washed with water (50 ml) and evaporated under reduced pressure. The residue was purified by trituration with hexane (3×25 ml), followed by column chromatography on silica gel (200 g) using an elution gradient of hexane:ethyl acetate (100:0 to 50:50), then crystallisation from hexane-dichloromethane, to give the title compound as a very pale grey solid. δ(CDCl$_3$): 5.46 (d,1H), 5.92 (d,1H), 6.63 (dd,1H), 7.51 (s,2H), 7.62 (s,1H). MS (thermospray): M/Z [M+NH$_4$] 315.0; C$_{12}$H$_6$Cl$_3$N$_3$+NH$_4$ requires 315.0.

What is claimed is:

1. A compound of formula (VII):

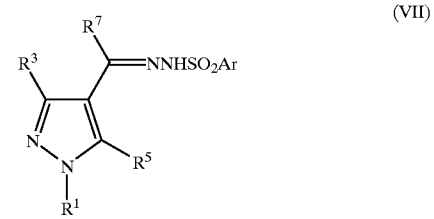

(VII)

wherein Ar is phenyl or naphthyl, either of which is optionally substituted with C$_1$ to C$_4$ alkyl, C$_1$ to C$_4$ alkoxy or halo;

R$^1$ is 2,4,6-trisubstituted phenyl wherein the 2- and 6-substituents are each independently selected from halo and the 4-substituents is selected from C$_1$ to C$_4$ alkyl optionally substituted with one or more halo, C$_1$ to C$_4$ alkoxy optionally substituted with one or more halo, S(O)$_n$C$_1$ to C$_4$ alkyl optionally substituted with one or more halo, halo and pentafluorothio; or 3,5-disubstitutes pyridin-2-yl wherein the 3-substituent is halo and the 5-substituent is selected from C$_1$ to C$_4$ alkyl optionally substituted with one or more halo, C$_1$ to C$_4$ alkoxy optionally substituted with one or more halo, S(O)$_n$C$_1$ to C$_4$ alkyl optionally substituted with one or more halo, halo and pentafluoro;

R$^3$ is cyano, C$_1$ to C$_5$ alkanoyl, phenyl, or is C$_1$ to C$_4$ alkyl optionally substituted with hydroxy or with one or more halo;

R$^5$ is hydrogen, C$_1$ to C$_4$ alkyl or halo; and

R$^7$ is hydrogen or C$_1$ to C$_4$ alkyl optionally substituted with one or more halo.

2. A compound according to claim 1 wherein Ar is 4-methylphenyl.

3. A compound according to claim 1 that is N-[3-Cyano-1-(2,6-dichloro-4-trifluoromethylphenyl)pyrazole-4-ylmethylidene]-N'-(4-methylphenylsulphonyl)hydazine.

* * * * *